(12) United States Patent
Holmen

(10) Patent No.: US 10,304,221 B2
(45) Date of Patent: May 28, 2019

(54) VISUALIZATION TECHNIQUES FOR DISPARATE TEMPORAL POPULATION DATA

(71) Applicant: Intermountain Invention Management, LLC, Salt Lake City, UT (US)

(72) Inventor: John R. Holmen, Park City, UT (US)

(73) Assignee: Intermountain Intellectual Asset Management, LLC, Salt Lake City, UT (US)

( * ) Notice: Subject to any disclaimer, the term of this patent is extended or adjusted under 35 U.S.C. 154(b) by 0 days.

(21) Appl. No.: 14/608,043

(22) Filed: Jan. 28, 2015

(65) Prior Publication Data

US 2015/0221110 A1    Aug. 6, 2015

Related U.S. Application Data

(60) Provisional application No. 61/934,594, filed on Jan. 31, 2014, provisional application No. 62/067,750, filed on Oct. 23, 2014.

(51) Int. Cl.
*G06Q 50/22* (2018.01)
*G06T 11/20* (2006.01)

(52) U.S. Cl.
CPC ........... *G06T 11/206* (2013.01); *G06Q 50/22* (2013.01)

(58) Field of Classification Search
CPC .. G06F 19/3443; G06F 19/3431; G06F 19/00; G06F 19/3456; G16H 50/70; G16H 10/20; G16H 50/20; G16H 50/30; G16H 50/50; Y02A 90/22; Y02A 90/26
See application file for complete search history.

(56) References Cited

U.S. PATENT DOCUMENTS

| | | | |
|---|---|---|---|
| 2005/0119534 A1* | 6/2005 | Trost | G06F 19/3456 600/300 |
| 2011/0191343 A1* | 8/2011 | Heaton | G06F 19/00 707/737 |
| 2012/0078601 A1 | 3/2012 | Avinash et al. | |
| 2014/0022255 A1 | 3/2014 | Barbouche et al. | |
| 2014/0079248 A1* | 3/2014 | Short | G10L 21/0272 381/119 |

OTHER PUBLICATIONS

Quackit, XML document 2013 Ben Fry, Visualizing Data 2008 Jon Peltier, Tornado Charts and Dot Plots., year 2008.*
University o f Georgia , Population modeling with dynamic models, Oct. 22, 2003.*
Quackit, XML document 2013 (Year: 2013).*
Ben Fry, Visualizing Data 2008 (Year: 2008).*
University of Georgia , Population modeling with dynamic models, Oct. 22, 2003 (Year: 2003).*

* cited by examiner

*Primary Examiner* — Devona E Faulk
*Assistant Examiner* — Ming Wu
(74) *Attorney, Agent, or Firm* — J. Richard Bucher; TechLaw Ventures, PLLC

(57) ABSTRACT

This patent application relates to Data visualization techniques for representing population data for a relatively large number of subjects associated with multiple populations. A graphical representation can be created to represent population data elements and corresponding population data values for the populations over time. The graphical representation can be utilized to analyze the populations.

19 Claims, 6 Drawing Sheets

PDGR 400

| Clinical Data Element | -F | -E | -D | -C | -B | -A | A | B | C | D | E | F |
|---|---|---|---|---|---|---|---|---|---|---|---|---|
| A1C | -0.41 | -0.56 | -0.41 | 1.973 | -0.6 | -0.3 | -0.37 | -0.62 | | | | |
| ALB | -0.58 | 32.3 | -0.63 | -0.03 | -0.15 | -0.03 | 0.486 | -0.41 | | | | |
| BUN | 95.33 | -0.51 | 0.361 | 0.334 | -0.06 | 0.262 | 0.631 | -0.06 | | | | |
| CHOL | -0.6 | -0.37 | -0.6 | -0.64 | -0.* | -.6 | -0.63 | -1 | | | | |
| PLT | -0.33 | 0.33 | 0.1 | -0.33 | -0.26 | 0.255 | -0.013 | -0.04 | | | | |
| RBC | | | -0.71 | | 0.42 | 0.189 | | -0.85 | -0.05 | | | |
| PCO2A | 0.23 | | 0.189 | 0.784 | 0.334 | 6.73 | 4.946 | -0.05 | | | | |
| PO2A | 0.189 | | 0.23 | 0.23 | 0.23 | 0.33 | 0.23 | 0.23 | 0.33 | | | |
| SEM (% Male) | | | -0.6 | -1 | -1 | | | -1 | | | | |
| CANCER | | | | -0.5 | | 0.189 | 0.189 | | | | | |
| CHF | | | -0.6 | | 2.568 | | | 1.973 | 1.973 | | | |
| DEMENTIA | | | -0.41 | 0.189 | | | 0.189 | 0.189 | 0.189 | | | |
| DIAB. (with Comp.) | 0.189 | | | -1 | | -1 | -1 | -0.6 | -0.1 | | | |

Timeline: 403
406
YEARS — MONTHS — WEEKS AND/OR DAYS — TZEOI — DAYS, HOURS, AND/OR MIN. — WEEKS AND/OR DAYS — MONTHS — YEARS
404
402
408
412
410

FIG. 4

VISUALIZATION TECHNIQUES FOR DISPARATE TEMPORAL POPULATION DATA

CROSS REFERENCE TO RELATED APPLICATION

This application claims the benefit of U.S. Provisional Application No. 61/934,594 filed Jan. 31, 2014 and U.S. Provisional Application 62/067,750 filed Oct. 23, 2014.

BACKGROUND

Visually organizing and depicting population data for a relatively large number of subjects of populations can assist clinicians and others to recognize relationships and trends. In addition to facilitating hypotheses and conclusions to be drawn, assessing such visually depicted data can also facilitate further manipulation and/or refinement of this data for further analysis. Current visualization techniques, however, do not provide for a sufficiently robust graphical representation.

SUMMARY

Data visualization techniques are described for representing population data (e.g., heterogeneous population data) for a relatively large number of subjects associated with two or more populations over time. By utilizing these techniques, previously unidentified (i.e., unrecognized) comparative population characteristics and possibilities associated with these populations can be identified and addressed.

In at least one embodiment, an interactive population data graphical representation (PDGR) can be created to represent (e.g., depict) population data that includes population data elements (PDEs) and/or PDE values, for two or more populations over time. A linear and/or non-linear timeline can be utilized to depict the PDEs and PDE values over a span of time. Each population may be associated with any number of subjects, such as individual patients, individual steps in a process, individual items, or the like. Once created, the PDGR can be utilized to analyze the populations. For example, the PDGR can be utilized to identify one or more comparative population characteristics and/or possibilities associated with the populations.

One or more actions can then be identified and/or implemented based on the analysis. For example, an action to address the identified comparative population characteristic(s) and/or possibility(ies) can be identified, and in some circumstances initiated. In other words, one or more actions can then be identified and/or implemented based on the identified comparative population characteristic(s) and/or possibility(ies).

In at least one embodiment, a clinical PDGR can be created and configured to depict population data that includes disparate patient PDEs for at least two patient populations over time. The clinical PDGR can be utilized to analyze the populations to identify one or more comparative population characteristics and/or possibilities associated with the patient populations. One or more clinical actions to address the identified comparative patient population characteristic(s) and/or clinical possibility(ies) can then be identified, and in some circumstances implemented.

In at least one embodiment, a process PDGR can be created and configured to depict population data that includes disparate process PDEs for at least two instances (e.g., cycles) of a process (i.e., method) over time. Each process instance can be considered a population that can be selected as a population of interest. Over a period of time (e.g., as represented by a timeline), the process PDGR can be utilized to analyze the populations to identify one or more comparative population characteristics and/or possibilities associated with the process.

BRIEF DESCRIPTION OF THE DRAWINGS

The accompanying drawings illustrate implementations of the concepts conveyed in the present application. Features of the illustrated implementations can be more readily understood by reference to the following description taken in conjunction with the accompanying drawings. Like reference numbers in the various drawings are used wherever feasible to indicate like elements.

FIGS. 4 and 5 illustrate an example population data graphical representation (PDGR) that may be implemented in accordance with at least one embodiment.

DETAILED DESCRIPTION

Overview

Figure 1:
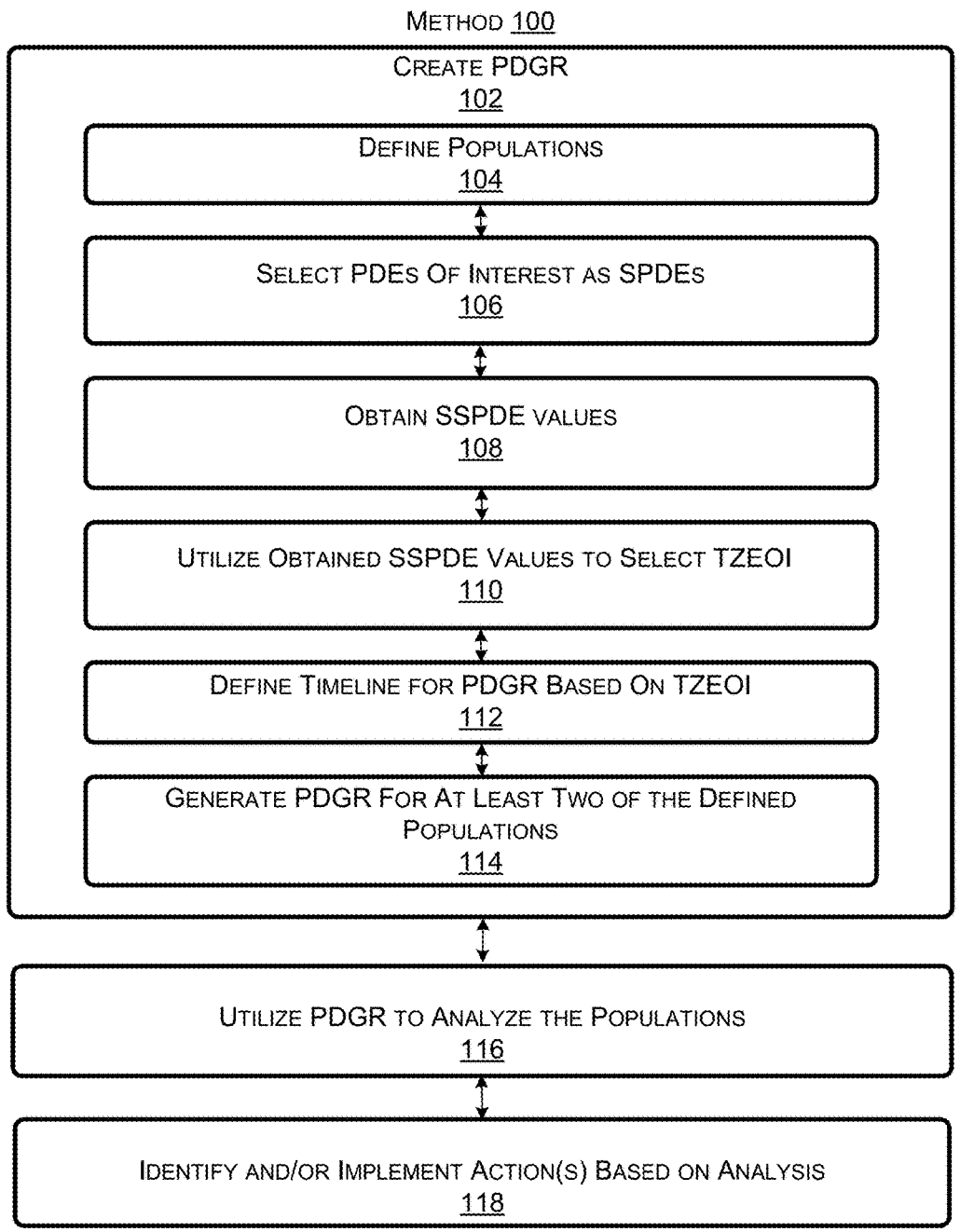
FIGS. 1 through 3 illustrate a flowchart of an example process, technique, or method that may be implemented, in accordance with at least one embodiment.

Data visualization techniques are described for representing population data (e.g., heterogeneous population data) with population data elements (PDEs) and/or PDE values for a relatively large number of subjects associated with two or more individual populations over time. By utilizing these techniques, previously unidentified (i.e., unrecognized) comparative population characteristics and possibilities associated with these populations can be identified and addressed.

In at least one embodiment, an interactive population data graphical representation (PDGR) can be created to depict population data, such as heterogeneous population data that includes heterogeneous PDEs and/or PDE values, for two or more defined populations over a span of time. For purposes of discussion, heterogeneous population data can mean data that: (i) includes quantitative and qualitative data about one or more populations and/or (ii) is obtained from multiple different sources and/or (iii) is obtained in multiple different formats.

Each defined population (i.e., population) may be associated with any number of subjects, such as individual patients, individual steps in a process, individual items, or the like. The PDGR can then be utilized to analyze the populations. For example, the PDGR can be utilized to analyze the populations to identify one or more comparative population characteristics (e.g. similarities and/or differences between the populations) and/or possibilities (e.g. opportunities and/or risks) associated with the populations.

One or more actions can then be identified, and in some circumstances initiated, based on the analysis. For example, an action(s) to address the identified comparative population characteristic(s) and/or possibility(ies) can then be identified, and in some circumstances initiated. In other words, an action(s) can then be identified and/or implemented based on the identified comparative population characteristic(s) and/or possibility(ies).

In at least one embodiment, multiple populations of interest can be defined. PDEs of interest for subjects of these populations can then be selected for the PDGR. A PDE that is selected for the PDGR can be referred to as a selected PDE (SPDE). SPDEs can be associated with any type of event (event type). More particularly, SPDEs can include information about (i.e., that describes) any type of event.

An individual subject of at least one of the defined populations can be associated with one or more individual SPDE values. An SPDE value for a certain subject can be associated with one or more corresponding SPDE events. More particularly, an SPDE value for a certain SPDE and individual subject can correspond to an SPDE event that occurred at a certain date and time. For purposes of discussion, an SPDE value for a certain SPDE and individual subject may be referred to herein as a subject-specific SPDE value (SSPDE value).

As a practical example, a certain type of laboratory (lab) test might be an SPDE. The data and time that the lab test was performed (e.g., taking a blood sample) and/or recorded for a certain individual subject might be an SPDE event for that SPDE. An SSPDE value for that the lab test, subject, and lab test performance might include one or more SSPDE value components specific to that subject and blood sample.

For example, without limitation, an SSPDE value might include the following SSPDE value components: an SSPDE subject identifier that identifies the subject, one or more SSPDE event descriptions that describe a certain SPDE event or events, one or more SSPDE event values that provide quantitative and/or qualitative information (e.g., results, measurements, etc.) about the subject and SPDE event(s), an SSPDE population code that identifies the subject with one or more of the defined populations, and one or more SSPDE event date and/or time stamps for each SPDE event description that indicate when each SPDE event was performed (e.g., when each lab test SPDE event for the subject was performed and/or recorded).

Once SPDEs are selected for the PDGR as SPDEDs, SSPDE values for some or all of the populations' individual subjects can then be obtained. In at least one embodiment, some or all of the SSPDE values can be directly obtained from obtained population data. Alternatively or additionally, some or all of the SSPDE values can be indirectly obtained from the population data by being derived from the population data. A time zero event of interest (TZEOI) associated with the populations and the obtained SSPDE values can then be selected by utilizing the obtained SSPDE values.

A common reference point, which may be referred to herein as time zero, for at least some of the obtained SSPDE values can then be determined based on the TZEOI and utilized to define a timeline. The TZEOI can thus serve as the common reference point for the obtained SSPDE values and time intervals of the timeline. For instance, individual time intervals of the timeline can be defined for the timeline relative to (e.g., before or after) the TZEOI. As such, for purposes of discussion, a TZEOI may also be referred to as a timeline common reference point.

For example, defining the timeline can include defining individual timeline time intervals (i.e., time intervals) for the PDGR based on the selected TZEOI. Individual time intervals occurring prior to the TZEOI can be defined as negative time intervals and time intervals occurring after the TZEOI can be defined as positive time intervals.

In at least one embodiment, a timeline time interval value (timeline TIV) can be calculated for, and assigned to, each time interval of the timeline. In other words, individual timeline TIVs can be calculated for, and assigned to, individual corresponding time intervals. The timeline TIV for a certain time interval can represent the time span, or range of time, for that certain time interval along the timeline. Negative time intervals might thus have a negative timeline TIV value (i.e., negative TIV) and positive time intervals might have a positive timeline TIV value (i.e., positive TIV).

Additionally, in at least one embodiment defining the timeline can also include defining a unit of measure (UOM) for each time interval of the timeline, and then assigning each UOM to its corresponding time interval. Without limitation, examples of a UOM include: decades, years, months, weeks, days, minutes, seconds, and the like.

In at least one embodiment, at least two of the time intervals of the timeline can each be measured in a different UOM. In such circumstances, the timeline is a non-linear timeline that corresponds to a non-linear scale. In some circumstances, most or all of the individual time intervals can be assigned different respective individual UOMs. In other words, a first UOM can be assigned to at least one time interval and at least one other UOM that is different than the first UOM can be assigned at least one other time interval. Therefore, at least two time intervals of the same timeline can be assigned different UOMs.

Once the timeline for the PDGR is defined, the PDGR with the SPDEs and timeline can then be generated for at least two of the defined populations by utilizing the obtained SSPDE values. For example, in at least one embodiment generating the PDGR can include calculating individual SSPDE TIVs for individual corresponding SSPDE values and appending each calculated SSPDE TIV to that SSPDE TIV's corresponding SSPDE value. In other words, for each SSPDE value of one or more of the obtained SSPDE values, an SSPDE TIV can be calculated and appended to that SSPDE value as an SSPDE value TIV component.

An SSPDE value's SSPDE TIV might, in some circumstances, be a value that can be mapped (i.e., matched) to a time interval's timeline TIV. As such, that SSPDE value can be mapped to that time interval by utilizing the SSPDE TIV and timeline TIV. For example, a time line's timeline TIV might include a range of TIV values (i.e., timeline TIV range). A first SSPDE value's SSPDE TIV might be a value within that timeline TIV range, and thus the first SSPDE value might be mapped to that time interval. A second SSPDE value's SSPDE TIV however might not be a value within that timeline TIV range, and thus that second SSPDE value might not be mapped to that time interval.

Once the SSPDE TIVs have been appended to their corresponding SSPDE values, generating the PDGR can include selecting (e.g., setting) an initial timeline width for the PDGR. The initial timeline width scale can represent the total span of time to be encompassed initially by the PDGR, and thus the timeline, when the PDGR is initially displayed.

In at least one embodiment, a PDGR tool (e.g., a timeline PDGR tool) can be utilized to select the initial timeline width scale and then, when desired, select one or more subsequent timeline width scales. In other words, the PDGR tool can be utilized to first set the timeline width scale as the initial timeline width scale and then re-set the timeline width scale any number of times thereafter as desired.

Generating the PDGR can also include creating a cell matrix dataset (CMD) of individual cells by preparing aggregated SSPDE values for at least some of the individual cells and then populating those cells with the aggregated SSPDE value(s). Other individual cells of the CMD can be populated with a null value or other type of value.

Once the TIVS are calculated and the CMD created, generating the PDGR can include determining one or more initial PDGR display attributes for the PDGR. Determining the initial PDGR display attribute(s) can include providing a set of default PDGR display attributes to be used by default. One or more of the default PDGR display attributes can then be changed as desired.

For example, in at least one embodiment a population PDGR display attribute can be utilized to identify at least two of the defined populations that have been selected to display in the PDGR. As another example, a population view PDGR display attribute can be utilized to identify an initial population view for the PDGR, such as a non-overlapping population view, partially-overlapping population view, or overlapping population view.

Once the initial PDGR display attribute(s) are determined, the CMD can be utilized to depict the PDGR based on the attribute(s). In at least one embodiment, this can be accomplished by depicting some or all of the SPDEs along a first axis of the PDGR and the timeline along a second axis of the PDGR. Each cell of the CMD (CMD cell), and thus each cell of the PDGR (PDGR cell), can be defined by the intersection of a corresponding SPDE and time interval. As such, each PDGR cell can be depicted at the intersection of that PDGR cell's corresponding SPDE and time interval. Additionally, each CMD cell, and thus PDGR cell, can be populated with either an aggregated SSPDE value or a null value.

In at least one embodiment, visual indicators that correspond to the aggregated SSPDE values and null values can then be attributed to the individual cells of the PDGR to create a heat map or other type of visual representation in the PDGR.

In at least one embodiment, one or more PDGR tools can be configured to create the PDGR, change (i.e. modify) the PDGR, and/or to analyze the populations (e.g., to identify one or more comparative population characteristics and/or possibilities for the populations). Additionally, one or more PDGR tools can be configured and utilized to identify and/or implement one or more actions based on the analysis of the populations. For example, the PDGR tool(s) can be configured and utilized to identify an action to address one or more identified comparative population characteristics and/or possibilities. For purposes of discussion, as used herein the term PDGR tool can include, in at least one embodiment, an interactive PDGR tool that can utilized and/or configured by a PDGR user or other individual.

For example, a population PDGR tool might be utilized to define populations for the PDGR, select SPDEs, obtain (e.g. extract) SSPDE values, identify a TZEOI (i.e., a timeline common reference point) associated with the populations, and/or define the timeline for the PDGR.

As another example, a display PDGR tool might be utilized to determine (e.g., select and/or re-select) one or more PDGR display attributes. For instance, a PDGR tool might be utilized to select a default PDGR display attribute as an initial PDGR display attribute and/or to change the PDGR display attribute by selecting another PDGR display attribute.

As yet another example, a PDGR tool may be utilized to alert or provide some other type of indication to a PDGR user that one or more similarities, differences, opportunities, and/or risks associated with the populations are identifiable in the PDGR, such as when the PDGR is created or manipulated.

In at least one embodiment, the PDGR and/or another type of data representation can be implemented in a system (e.g., a data representation system) of one or more computing devices and/or one or more networks. The system might include, for instance, the PDGR and PDGR tools (e.g., one or more of the PDGR tools described herein). In some circumstances, the system might also include one or more other PDGRs and/or other type or types of graphical representations. Alternatively or additionally, the system might also include one or more other PDGR tools and/or other type or types of graphical representation tools.

In at least one embodiment, a clinical PDGR can be created and configured to depict population data that includes disparate patient PDEs for at least two patient populations over time. The clinical PDGR can be utilized to analyze the populations to identify one or more comparative population characteristics and/or possibilities associated with the patient populations. One or more clinical actions to address the identified comparative patient population characteristic(s) and/or clinical possibility(ies) can then be identified, and in some circumstances implemented.

In at least one embodiment, a process PDGR can be created and configured to depict population data that includes disparate process PDEs for at least two instances (e.g., cycles) of a process (i.e., method) over time. Each process instance can be considered a population that can be selected as a population of interest. Over a period of time (e.g., as represented by a timeline), the process PDGR can be utilized to analyze the populations to identify one or more comparative population characteristics and/or possibilities associated with the process.

For example, a risk point and/or possible process improvement opportunity associated with the process can be recognized. One or more process-related actions to address the identified comparative population characteristic(s) and/or possibility(ies) can then be identified, and in some circumstances implemented. For example, a change to the process can be made to eliminate or mitigate the identified risk point and/or to realize the process improvement opportunity.

Multiple and varied implementations are described herein. Generally, any of the features/functions described with reference to the figures can be implemented using software, hardware, firmware (e.g., fixed logic circuitry), manual processing, or any combination thereof. The terms "module", "tool", and/or "component" as used herein may generally represent software, hardware, firmware, or any combination thereof. For instance, the terms "tool" and "module" can represent software code and/or other types of instructions (e.g. a software application) that can be configured and utilized to perform specified tasks when executed on a computing device or devices.

Generally, the illustrated separation of modules, tools or components and functionality into distinct units may reflect an actual physical grouping and allocation of such software, firmware, and/or hardware. Alternatively or additionally, this illustrated separation can correspond to a conceptual allocation of different tasks to the software, firmware, and/or hardware. Furthermore, it is to be appreciated and understood that the illustrated modules, tools, and/or components and functionality described herein can be located at a single site (e.g., as implemented by a computing device), or can be distributed over multiple locations (e.g., as implemented over multiple computing devices).

Example Process, Technique, or Method

As explained above, by utilizing the described data visualization techniques, a PDGR can be created and utilized to identify previously unrecognized comparative population characteristics and possibilities associated with two or more populations. In this regard, the PDGR can be configured to depict population data, including disparate SPDEs associated with at least two populations of interest over time. In some circumstances, one or more actions based on these characteristics and/or possibilities can be identified, and in some circumstances implemented.

To facilitate the readers' understanding, FIG. 1 illustrates an example flowchart of a process, technique, or method 100 that is consistent with at least one implementation of the described data visualization techniques. For ease of discussion, the process, technique, or method 100 will be described in the context of a PDGR, such as described herein. However, it is to be appreciated and understood that this process, technique, or method is not necessarily limited to a PDGR, and any type of suitable data representation may be implemented and utilized in accordance with the described techniques.

Note that the order in which the blocks of process, technique, or method 100 are described is not intended to be construed as a limitation and any number of the described blocks or acts can be combined in any order and performed any number of times.

Furthermore, the process, technique, or method 100 can be implemented in any suitable hardware, software, firmware, or combination thereof such that one or more computing devices can implement the process, technique, or method 100 and/or cause the process, technique, or method 100 to be implemented.

In at least one circumstance for instance, the process, technique, or method 100 can be stored on one or more computer-readable storage media as a set of computer-readable instructions that, when executed on a computing device(s), causes all or part of the process, technique, or method 100 to be performed.

Referring to process, technique, or method 100, at block 102 an interactive PDGR can be created. In operation, any suitable process, technique, or method can be utilized to create the PDGR. For example, to facilitate the readers' understanding, here at block 104 multiple populations for the PDGR can be defined. Each defined population can be a summation of, or otherwise representative of, any number of subjects and can be associated with any number and type of population data for (e.g., about) that defined population's subjects, and thus any number and type of PDEs about those subjects. In at least some circumstances, a defined population might include at least one subject in common with one another defined population. For example, one defined population might be a subset one or more other defined populations.

Each of the populations can be defined in any suitable way. In at least one embodiment for instance, a PDGR tool (e.g. PDGR population definition tool) can be utilized to perform some or all of this task. Additionally, each of the populations can be defined based on any type or types of criteria. For instance, a population can be defined by utilizing computer-implemented functionality to assess the type and scope of data described in an article or other document, or that may be available in a data repository for instance. A population can be defined based on an idea, notion, topic of interest, and/or question that a PDGR user might have.

As a practical non-limiting example, consider a data repository (e.g., clinical enterprise data warehouse (EDW)) that includes clinical population data about a number of patients. These clinical population data might include clinical information about individual patients in the form of individual SPDEs and/or individual SSPDE values. Each patient can be considered a subject of one or more of the defined populations, and this a subject of the defined populations. For instance, one or more SSPDE values for a certain SPDE and patient (i.e., subject) can correspond to one or more certain SPDE events that each occurred at a certain date and time.

Continuing with this example, two distinct individual populations, each including a cohort of the patients identified in the repository, can be defined based on a general inquiry about why some hip surgery patients had an extended hospital stay following their surgery while some other hip surgery patient did not have an extended hospital period.

More particularly, a first patient population of a relatively large cohort of the patients who have had hip surgery can be defined. The subjects of this first population are the patients in this relatively large cohort. A second population of a relatively smaller cohort of the patients who had hip surgery without an extended hospitalization period can also be defined. The subjects of this second population are the patients in this relatively smaller cohort.

Note that in this particular example, the first population has subjects in common with the second population. In fact, the second population is a subset of the first population. As such, each subject of the second population also belongs to the first population. This is not to be interpreted as being limiting however, and in at least some circumstances two defined populations might not have any subjects in common, or might only have some subjects in common.

Referring back to process, technique, or method 100, once the populations are defined at block 104, at block 106 SPDEs for the PDGR can be selected as SPDEs. In other words, PDEs of interest for the populations' subjects can then be selected as SPDEs. As explained above, an individual subject of at least one of the populations can be associated with one or more SSPDE values.

PDEs can be selected as SPDEDs in any suitable way and based on any suitable criteria. For example, an individual PDE might be selected as an SPDED by a PDGR user (e.g., utilizing a PDGR tool) by the user first considering the criteria used to define the populations and then selecting that individual PDE based on it being associated with (e.g., related to) that criteria.

Once the SPDEs are selected at block 106, at block 108 SSPDE values can be obtained from one or more sources. More particularly for instance, SSPDE values can be directly or indirectly obtained from population data obtained from the source(s). As explained above, these obtained SSPDE values can be for individual subjects of the defined populations. More particularly, individual obtained SSPDE values can correspond to individual subjects of the defined populations.

As will be appreciated and understood by those skilled in the art, the SSPDE values can be obtained at block 108 directly and/or indirectly from the sources(s) in any suitable way. For example, in at least one embodiment, obtaining can be accomplished by extracting population data that includes SSPDE values (i.e., extracted SSPDE values). The extracted SSPDE values can thus be directly obtained from the population data. In at least one embodiment, some or all of these extracted population data can include heterogeneous population data. In other words, in at least some circumstances population data extracted from the source(s) can be heterogeneous population data that includes individual heterogeneous SSPDE values.

Alternatively or additionally, SSPDE values can be calculated or otherwise derived from extracted population data (i.e., derived SSPDE values). In such circumstances, the derived SSPDE values have still been indirectly obtained from the population data. In at least one embodiment, some or all of these extracted population data can include heterogeneous population data. In other words, in at least some circumstances population data extracted from the source(s) can include heterogeneous population data.

In at least one embodiment, obtaining extracted SSPDE values can include an extraction, transformation and load (ETL) process in which population data that includes SPDEs is extracted from the source(s), transformed into individual extracted SSPDE values, and loaded into a PDGR-accessible source that can be utilized to generate the PDGR. Alternatively or additionally, in at least one embodiment obtaining extracted SSPDE values can include extracting population data that includes SSPDE values from the source(s) without transforming and/or loading.

As explained above, SSPDE values obtained at block 108 can include any type of subject-specific information in any suitable form(s) or format(s). For example, an SSPDE value might include individual SSPDE value components that describe the SSPDE value and provide quantitative and/or qualitative information about a certain subject and SPDE event(s). The SSPDE value component examples described above, for instance, can include: an SSPDE subject identifier, SSPDE event description, SSPDE event value, SSPDE population code, and SSPDE event date and/or time stamp. Additionally, an SSPDE value component might be an SSPDE TIV that has appended to an SSPDE value, as described below.

To facilitate the reader's understanding, as a simple practical example consider an SSPDE value for a patient "X" who had a glycated hemoglobin (HbA1c) level taken of "53 mmol/mol (DCCT 7%)" on 12/12/2014 at 8 AM in the morning. Assume that two populations, designated with population codes "1" and "2", respectively, were defined. Also, assume that patient "X" belongs to both of the defined populations. An SSPDE value for this patient and AIC level SPDE event might include the following obtained SSPDE value components:

SSPDE subject identifier: "X",
SSPDE event description: "Clinical lab value-HbA1C",
SSPDE event value: "53 mmol/mol (DCCT 7%)",
SPDE population code: "1, 2",
SPDE event date and/or time stamp: "12/12/2014, 0800".

It is to be appreciated and understood that this is one non-limiting example, and as will be appreciated and understood by those skilled in the art, SSPDE values can include any type of subject-specific information in any suitable form(s) or format(s).

As noted above, in at least one embodiment a PDGR tool (e.g., PDGR extraction tool) can be utilized to obtain (e.g., extract and/or derive) SSPDE values. For example, the PDGR tool might be utilized to find and select SSPDE values and/or other population data at the source(s), copy this population data from the source(s) to a PDGR-accessible target location, and store the copied population data at the target location.

While in some circumstances this process might require little or no manipulation (i.e. transformation) of the population data elements, in other circumstances one or more types of transformation processes might be necessary to meet the technical requirements of the target location. One transformation type might be, for instance, to calculate or otherwise derive SSPDE values from SPDE data and/or other population data copied from the source(s). In at least one example, the PDGR tool might be configured to utilize a PDGR extraction algorithm (e.g., ETL algorithm) to perform some or all of this process.

At block 110, the obtained SSPDE values can be utilized to select a time zero event of interest (TZEOI). The TZEOI can be selected in any suitable way. For example, SSPDE components can be utilized to identify an event of interest (EOI) that is common to some or all of the subjects of the defined populations.

In at least one embodiment, individual SSPDE event descriptions, SSPDE population codes, and/or SSPDE event time and/or date stamps can be evaluated to identify an SPDE event that is an EOI to serve as the TZEOI. In other words, one or more SSPDE values can be evaluated to identify an SPDE event that is an EOI to serve as the timeline common reference point for the timeline. The TZEOI can thus be a certain type of event (i.e., an event type) that is associated with the obtained SSPDE values and/or SPDE types. As such, in at least one embodiment the TZEOI can be a certain SPDE event type selected from the various SPDE event types associated with the obtained SSPDE values.

Furthermore, the TZEOI can be identified based on any type of criteria. For example, the TZEOI might be identified by virtue of being associated with the basis for defining the two or more populations. In other words, the TZEOI might be selected, for instance, based on the idea, notion, topic of interest, and/or question associated with the basis for defining the populations.

From a practical perspective, another criterion might be that the TZEOI represents a SPDE type that is common to all or most of the subjects in the defined populations. In at least one embodiment for instance, an event (e.g., SPDE event) that is common to all of the subjects can be selected as the TZEOI. By virtue of being common to most or all of the individual subjects of the defined populations, the TZEOI can serve as a common reference point, which may be referred to as time zero, for most or all the subjects in the defined populations. With respect to each subject, the date and time of the TZEOI's occurrence for each subject can thus serve as a reference date and/or time for SSPDE values, aggregated SSPDE values as described below, and corresponding SPDE events for that subject.

The TZEOI can be any event type. For example, in the context health care, the TZEOI might be a treatment event type (e.g., surgery or other type of procedure, hospitalization, clinic visit, etc.), a clinical observation or result event type (e.g., clinical assessment score, lab test result value, etc.), or the like. As another non-limiting example, in the context of a process, the TZEOI might be a certain activity or method type (e.g., a series of related manufacturing or processing steps or activities, a quality control check, a shift change, etc.), a certain point or points along the process, or the like.

As a practical example, recall the non-limiting example above where two hip surgery patient populations are defined: a first patient population of patients who have had hip surgery, and a second patient population of patients without an extended hospital stay. In this example, each patient can be considered a subject of one or both of the two defined hip surgery patient populations. The TZEOI, when identified based on the general inquiry about why some hospitalized hip surgery patients have an extended period of stay in the hospital compared to others, might be the hip surgery event.

Note that from a practical perspective, in this example the TZEOI is an event type that is common to all of the patients (i.e., subjects) in the two defined hip surgery patient populations since each patient had hip surgery. In other words, in this example, each patient had at least one hip surgery (the TZEOI) at a certain date and time. Thus, the date and time of each individual subject's hip surgery can serve as a reference date and/or time for one or more obtained SSPDE values for that patient. As noted above, in at least one embodiment, a PDGR tool (e.g., timeline PDGR tool and/or population PDGR tool) can be utilized to identify a TZEOI associated with the populations.

At block 112, a timeline for the PDGR can be defined based on the TZEOI identified at block 110. More particularly for example, the timeline can be defined by utilizing the TZEOI as a common reference point, or time zero, for the timeline. In at least one embodiment, to define the timeline, individual time intervals can be defined for the timeline relative to (e.g. before or after) the TZEOI. In other words, time intervals for the timeline can be defined based on the common reference point that is the TZEOI.

Individual time intervals can define, and thus represent, a time span that forms a portion of the entire time span of the timeline. For example, each time interval can be defined by a pair of two points along the timeline, such as a first point and last point (e.g. 5 years to 10 years), that form the time span, or range of time, for that individual time interval. Any number of SPDEs to be displayed in the PDGR may occur with an individual time interval. In other words, any number of SPDEs can correspond to a certain time interval of the timeline.

The timeline can be defined at block 112 in any suitable way. For example, in at least one embodiment individual time intervals for the PDGR can be defined by a timeline TIV and UOM for that time interval. More particularly, a timeline TIV can be calculated for, and assigned to, each time interval. In other words, defining a time interval can also include calculating a timeline TIV for that time interval and assigning the timeline TIV to that time interval.

The timeline TIV for a certain time interval can represent the time span, or range of time, for that certain time interval along the entire timeline of the PDGR. Negative time intervals might thus assigned a negative timeline TIV value and positive time intervals assigned a positive timeline TIV value. Accordingly, a time interval occurring prior to the TZEOI can be defined as a negative time interval and time interval occurring after the TZEOI can be defined as a positive time interval.

For example, a time interval's timeline TIV might be the pair of two points along the timeline that form the time span for that individual time interval accompanied by a negative or positive indicator to indicate the time line's position relative to the TZEOI along the timeline. The time span, or range of time, for a certain time interval can be represented by the timeline TIV for that time interval. For example, a time interval's timeline TIV might be a pair of two points along the timeline accompanied by a negative or positive indicator to indicate the time line's position relative to the TZEOI along the timeline.

Additionally, a UOM can be attributed to a certain time interval and used as the UOM for measuring the time span, or range of time, for that certain time interval. An individual time interval's UOM might be measured in years, months, days, hours, minutes, seconds, or any other UOM. In other words, defining a time interval can also include attributing a UOM to that time interval.

As noted above, in at least one embodiment at least two of the time intervals of the timeline can be measured in a different UOM. In other words, at least two of the time intervals of the timeline might not be attributed the same UOM. When one or more individual time intervals of a timeline are not measured in the same UOM, the timeline corresponds to a non-linear scale. In such a circumstance, the timeline is a non-linear timeline that includes at least two individual time intervals that are each measured in a different UOM.

As such, in accordance with the described techniques, in at least one embodiment the time span for a first time interval of the timeline can be measured differently (i.e., by a different UOM) than the time span of a second time interval of the timeline. For example, the first time interval might represent a time span that is measured in years or decades, and the second time interval might represent a time span that is measured in days, hours, or minutes.

Non-limiting examples of time intervals that can occurring prior to time zero, at time zero (and thus during the TZEOI), or after time zero can include: minutes before and/or after time zero (e.g., measured in a UOM of minutes), hours before and/or after time zero (e.g., measured in a UOM of hours), days before and/or after time zero (e.g., measured in a UOM of days), weeks before and/or after time zero (e.g., measured in a UOM of weeks), months before and/or after time zero (e.g., measured in a UOM of months), or years before and/or after time zero (e.g., measured in a UOM of years.

Individual time intervals of a PDGR timeline can be organized (e.g. depicted and/or arranged) in the PDGR in any suitable manner. For example, in at least one embodiment individual time intervals can be sequentially organized in the PDGR as part of the timeline based upon time zero (and thus based upon the TZEOI). As noted above, individual time intervals occurring prior to the TZEOI might be defined as negative time intervals and time intervals occurring after the TZEOI might be defined as positive time intervals. In at least one embodiment, individual time intervals can be depicted in the PDGR as part of the timeline.

As noted above, in at least one embodiment a PDGR tool (e.g., timeline PDGR tool) can be utilized to define the timeline at block 112.

Referring back to FIG. 1, once the timeline for the PDGR is defined at block 112, at block 114 the PDGR can be generated for at least two of the defined populations. This can be accomplished in any suitable way. For example, in accordance with at least one embodiment, the process, technique, or method 200 illustrated in FIG. 2 and described below can be utilized to accomplish block 114.

Note that the order in which the blocks of process, technique, or method 200 are described is not intended to be construed as a limitation, and any number of the described blocks or acts can be combined in any order and performed any number of times.

Furthermore, process, technique, or method 200 can be implemented in any suitable hardware, software, firmware, or combination thereof such that one or more computing devices can implement the process, technique, or method 200 and/or cause the process, technique, or method 200 to be implemented.

In at least one circumstance for instance, the process, technique, or method 200 can be stored on one or more computer-readable storage media as a set of computer-readable instructions that, when executed on a computing device(s), causes all or part of the process, technique, or method 200 to be performed.

Figure 2:
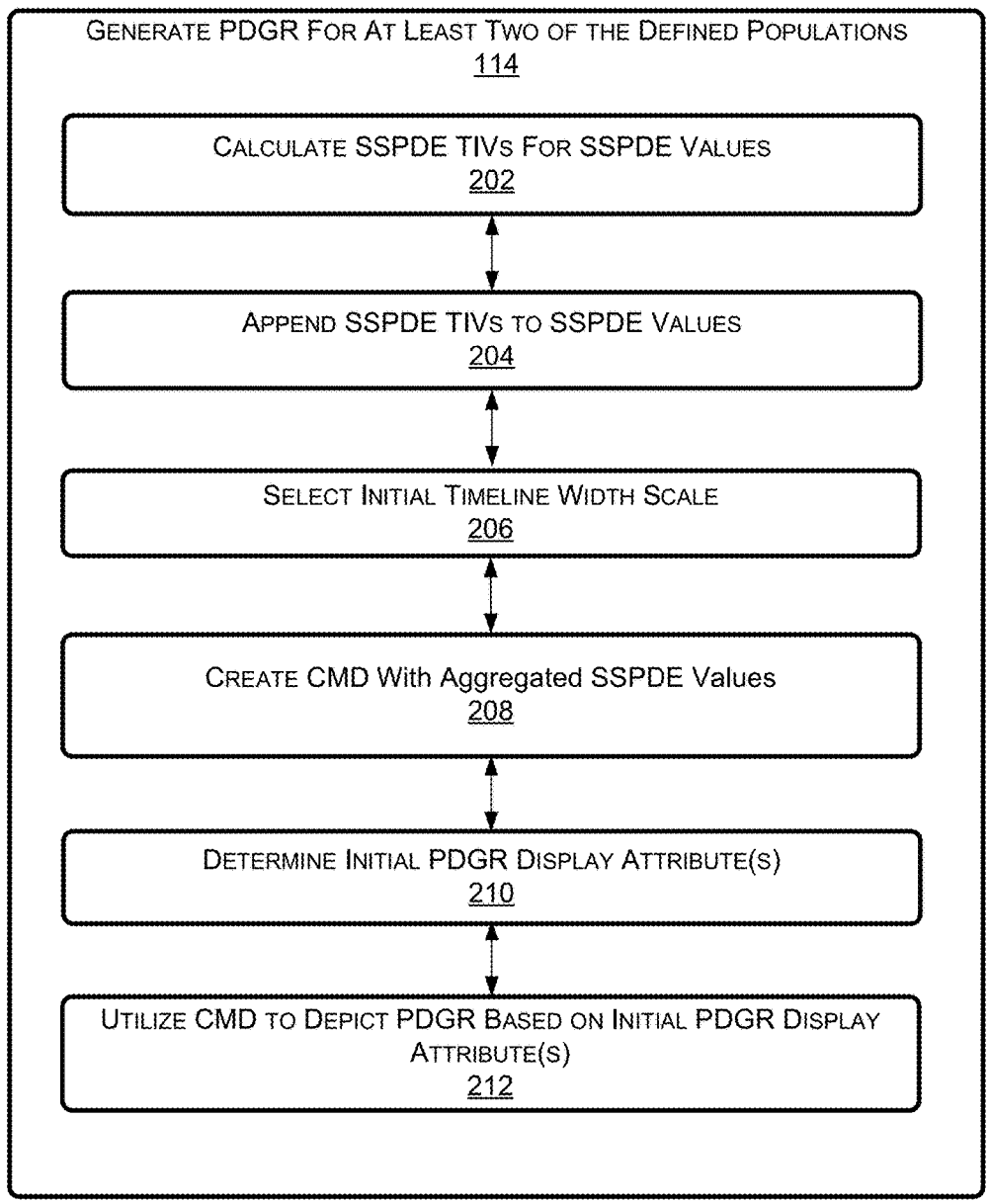

Referring now to FIG. 2, at block 202 TIVs for the SSPDE values can be calculated. For purposes of discussion, a TIV calculated for an SSPDE value may be referred to as an SSPDE TIV. More particularly, individual SSPDE TIVs can be calculated for individual corresponding SSPDE values. In at least one embodiment, an individual SSPDE TIV for a corresponding individual SSPDE value can be calculated by utilizing the SSPDE value's SPDE event date and/or time stamp component to determine a date and/or time for the SSPDE value.

An SSPDE TIV might, in some circumstances, be a value that corresponds to a timeline TIV. For example, as explained above, in at least one embodiment the time span, or range of time, for a certain time interval can be represented by the timeline TIV for that time interval. An SSPDE TIV that is calculated for a certain SSPDE value might, therefore, be a value within the range of TIV values for that certain time interval. In this regard, note that in some circumstances, multiple SSPDE TIVs calculated for multiple different corresponding SSPDE values might include two or more SSPDE TIVs that correspond to the same timeline TIV. Alternatively, that SSPDE TIV might be a value that is not within the range of TIV values for that certain time interval.

In at least one embodiment, an SSPDE TIV can be calculated for each SSPDE value obtained at block 108. In at last one other embodiment however, an SSPDE TIV might not be able to be calculated for every SSPDE value obtained at block 108.

At block 204, the SSPDE TIVs calculated at block 202 can be appended to the SSPDE values. This can be accomplished in any suitable way. For example, as noted above, in at least one embodiment an individual SSPDE TIV calculated for a corresponding SSPDE value can be appended to that SSPDE value as an additional SSPDE value component (e.g., SSPDE TIV). Alternatively or additionally, a table or other type of crosswalk might be utilized to link individual SSPDE values to individual corresponding calculated SSPDE TIVs for instance.

At block 206 an initial timeline width scale for the PDGR can then be selected (e.g., set). The initial timeline width scale can represent the total span of time to be encompassed initially by the PDGR when the PDGR is initially displayed.

In at least one embodiment, the timeline PDGR tool can be utilized to select the initial timeline width scale and then, when desired, select one or more subsequent timeline width scales. In other words, the PDGR tool can be utilized to set the timeline width scale as the initial timeline width scale, and then to change the initial timeline width scale any number of times thereafter as desired.

As will be appreciated and understood, in at least one embodiment selecting the initial timeline width scale might, in some circumstances, affect the time span, and thus potentially the timeline TIV, of one or more of the time intervals of the timeline defined at block 112. For example, selecting a timeline width scale might cause two time intervals on each end of the timeline relative to the TZEOI (i.e. a negative time interval at one end and a positive time interval at the other end) to be truncated. In such circumstances, in at least one embodiment the timeline TIVs of each of the affected time interval(s) can be adjusted at least in part automatically by utilizing the timeline PDGR tool.

Recall that any of the blocks of process, technique, or method 100 can be combined in any order and performed any number of times. As such, in at least one embodiment block 206 might be performed prior to block 210 described below. Alternatively, in at least one embodiment block 206 might be performed during block 210. For example, block 206 might be performed as part of 210.

At block 208 a CMD with aggregated SSPDE values for the PDGR can be created. The CMD can include multiple CMD cells, one or more of which can be depicted as a PDGR cell in the PDGR. More particularly, for each of the two or more populations to be depicted in the PDGR, an individual CMD cell that corresponds to a certain SPDED and time interval can be depicted in the PDGR as a PDGR cell. As such, for purposes of discussion, CMD cells that correspond to an SPDED can be depicted as PDGR cells, and thus may be referred to herein as PDGR cells.

The CMD can be created in any suitable way. For example, in at least one embodiment individual SSPDE values can be mapped (i.e. matched) to corresponding SPDEs (including one or more SPDEDs) and time intervals. More particularly, the SSPDE event description component of each SSPDE value can be mapped to a corresponding SPDE. In other words, each SSPDE value can be mapped to corresponding SPDE by utilizing that SSPDE value's SSPDE event description component.

Similarly, the SSPDE TIV for each SSPDE value can also be mapped to a corresponding timeline TIV of a time interval, and thus to that time interval. In other words, each SSPDE value can be mapped to corresponding time interval by utilizing each SSPDE value's SSPDE TIV and the timeline TIVs of the timeline's time intervals. By virtue of being mapped to a certain SPDE and time interval, each SSPDE value can thus also be mapped to a certain CMD cell that corresponds to that SPDE and time interval.

Once each SSPDE value has been associated with an individual SPDE and time interval, and thus with an individual CMD cell, an aggregated SSPDE value can be calculated for each of one or more CMD cells based on each CMD cell's on the one or more individual SSPDE values. In other words, one or more individual aggregated SSPDE values can be calculated for one or more individual corresponding CMD cells. Each CMD cell for which an aggregated SSPDE has been calculated can then be populated with that CMD cell's corresponding calculated aggregated SSPDE value.

Aggregated SSPDE values can be calculated and populated in corresponding CMD cells in any suitable way. For example, in at least one embodiment an aggregation method can be utilized to calculate the aggregated SSPDE values for CMD cells associated with at least one SSPDE value. Each aggregated SSPDE value for a CMD cell can be calculated based on that CMD cell's one or more SSPDE values and corresponding SSPDE value components. Each CMD cell with at least one SSPDE value for which an aggregated SSPDE value has been calculated can then be populated with that aggregated SSPDE value. Thus, for a CMD cell associated with multiple SSPDE values, that CMD cell can be populated with an aggregated SSPDE value that is based on the SSPDE value components of each of the multiple SSPDE values.

Each CMD cell that is not associated with at least one SSPDE value can be populated with a with a null value (e.g. zero) instead of an aggregated SSPDE value. A null value populated to a CMD cell can indicate that there is not at least an aggregated SSPDE value for that CMD cell. In other words, those CMD cells, if any, for which at least one aggregated SSPDE value has not been prepared can be populated with a null value (e.g. zero) which indicates that there is not a corresponding aggregated SSPDE value.

For example, an individual CMD cell might correspond to a certain individual SPDE and time interval. However, the SSPDE values obtained at block 108 might not include any SSPDE values for any subjects that correspond to that certain individual SPDE and time interval. In such a situation, that individual CMD cell might be populated with a null value to indicate that no there is not an aggregated SSPDE value for that cell.

An aggregated SSPDE value can represent a combination of one or more individual SSPDE values that correspond to a certain individual SPDE and time interval. An aggregated SSPDE value can include any type and quantity of individual SSPDE values and/or other data (e.g., metadata) in any suitable format.

For example, an aggregated SSPDE value can include multiple SSPDE values for multiple subjects, each included SSPDE value of the aggregated SSPDE value being associated with the same SPDED and having an SSPDE TIV associated with the same time interval of the timeline. Alternatively or additionally, an aggregated SSPDE value can include at least one numerically aggregated value of multiple SSPDE values, such as a sum value, mean value, difference value, average value, or the like. Additionally, in at least one embodiment an aggregated SSPDE value can include metadata, such as additional data about one or more of the individual SSPDE values.

Assume, for instance, that the two SSPDE values correspond to a first defined population and second defined population, respectively. This comparison might be expressed and represented in a ratio, percentage, and/or other type of comparative form in the aggregated SSPDE value. As such, a certain aggregated SSPDE value associated with a PDGR cell might represent a comparatively larger difference between two SSPDE values associated with that cell than the difference between two other SSPDE values represented by another aggregated SSPDE value associated with a another PDGR cell.

As a practical example, consider an aggregated SSPDE value that provides a comparison of two SSPDE values (e.g., a difference of two or more SSPDE event value components) associated with a certain individual cell of the CMD, and thus of the PDGR. In at least one embodiment for instance, a difference function can be utilized to calculate a difference value for the two SSPDE values. An example of a difference function associated with two populations, population A and B, might be f(x)Cell=f(Pop. A (cell)–Pop. B(cell)).

Consider, for instance, a difference function PDGR (cell X)=f(Pop. A (CMD cell X)–Pop. B(CMD cell X)), where PDGR (cell X) might correspond to the aggregated SSPDE value for a PDGR cell X. In one example, Pop. A (cell) might be an average of all of population A subject's BUN values for the CMD cell X. Pop. B (cell) might be an average of all population B subject's BUN values for the CMD cell X. PDGR (cell X) would thus be the difference in BUN average values of the two populations (population A and B).

An aggregated SSPDE can be created in any suitable way. For example, in at least one embodiment a cell aggregation method (CAM) can be utilized to prepare (e.g., assimilate, calculate, etc.) aggregated SSPDE values for the CMD. For instance, individual one or more individual SSPDE value components (e.g., SSPDE event value component(s)) might be utilized to calculate an aggregated SSPDE value (e.g., by utilizing a difference function).

Furthermore, in some circumstances the CAM and/or another means can be utilized to prepare additional metadata to be included in one or more of the aggregated SSPDE values. In other words, in at least one embodiment metadata about one or more of the SSPDE values can be included with the SSPDE value(s) as part of an aggregated SSPDE value associated with the SSPDE value(s).

In at least one embodiment, in addition to aggregated SSPDE values and null values, cell aggregated metadata (CAM) can be calculated for one or more CMD cells based, at least in part, on each such CMD cell's aggregated SSPDE value or null value. Each CMD cell for which CAM has been calculated can then be populated with that CAM. CAM for a CMD cell can provide additional information about that CMD cell than might be otherwise readily apparent from viewing that CMD cell as a PDGR cell in the PDGR.

For example, CAM for a CMD cell populated with an aggregated SSPDE value might include metadata about the aggregation method utilized to calculate that aggregated SSPDE value. For example, the aggregation method might include a comparison function utilized to compute a comparison of two SSPDE values (e.g., a comparison of two SSPDE event value components) associated with a certain individual cell of the CMD, and thus of the PDGR. This comparison might be included as part of that CMD cell's aggregated SSPDE value.

As another example, the aggregation method might include one or more other functions utilized to compute details about that CMD cell's corresponding time interval UOM, and/or other cell characteristic(s) not all visually depicted by default in the PDGR.

Once the TIVS are calculated and the CMD created, at block 210 one or more initial PDGR display attributes can be determined. The initial PDGR display attribute(s) can be determined in any suitable way. For example, in at least one embodiment determining the initial PDGR display attribute(s) can include providing a set of default PDGR display attributes to be used by default. One or more of the default PDGR display attributes can then be changed as desired.

For example, in at least one embodiment a population PDGR display attribute might be utilized to identify at least two of the defined populations that have been selected to display in the PDGR. As another example, a population view PDGR display attribute might be utilized to identify an initial population view for the PDGR, such as an non-overlapping population view, partially-overlapping population view, or overlapping population view for instance.

To accomplish block 210, in at least one embodiment one or more PDGR tools can be utilized. For example, a PDGR tool can be utilized to select a population PDGR display attribute that indicates at least two of the defined populations that are populations of interest to display in the PDGR. For purposes of discussion, a defined population that is selected to display in the PDGR may be referred to as population to display. For instance, a default population PDGR display attribute might have two of the defined populations selected by default as the populations to display. The PDGR tool can then be utilized to change one or both of the default populations to display when desired.

As another example, a PDGR tool (e.g., a population display PDGR tool) can be utilized to select a population view PDGR display for the PDGR. More particularly for instance, PDGR cells that correspond to a certain population to display might be depicted separately from other PDGR cells that correspond to the other population(s) to display (i.e., non-overlapping population view), partially overlapping with the other cells (i.e., partially-overlapping population view), or completely overlapped with the other cells (i.e., overlapping population view). In at least one embodiment, a default population view PDGR display attribute might be set for a certain population view, such as non-overlapping population view for instance.

As another example, a PDGR tool (e.g., a SPDE PDGR tool) can be utilized to change an SPDE PDGR display attribute in order to select some or all of the SPDEDs to be depicted (i.e., displayed) in the PDGR. In at least one embodiment, a default setting of the SPDE PDGR display attribute might identify all of the SPDEDs to be depicted in the PDGR. The PDGR tool might then me utilized change the default setting of the SPDE PDGR display attribute to filter out one or more of the SPDEDs for depiction in the PDGR when desired, or to select one or more additional PDEs of interest selected at block 106 as SPDEDs.

As another example, a PDGR tool (e.g., a timeline PDGR tool) can be utilized to change a time interval PDGR display attribute to select the UOM to be used for one or more of the individual time intervals of the timeline. In at least one embodiment, a default UOM for a certain time interval might be the UOM that was utilized to define that time interval. Collectively, the default UOMs of the timeline can be used define the default timeline instance for the PDGR.

The PDGR tool can also be utilized to then change the UOM of one or more of the individual time intervals, and thus to change the default timeline instance, and/or a current timeline instance, when desired. As such, any number of additional linear and/or non-linear timeline instances for the PDGR might be selected as desired. In other words, the PDGR tool might be utilized to switch between multiple possible timeline instances, including one or more linear and/or non-linear timeline instances.

As another example, a PDGR tool (e.g., the SPDE PDGR tool) can be utilized to change the SPDE PDGR display attribute in order to arrange and/or rearrange individual SPDEs to be displayed in the PDGR in any suitable manner. In other words, the PDGR tool can be utilized to change the arrangement of one or more individual SPDEDs in the PDGR. For instance, the PDGR to might be utilized to change the arrangement of two or more of the SPDEDs with respect to (i.e., relative to) one another. Alternatively or additionally, the PDGR tool might be utilized to change the arrangement of two or more of the SPDEDs with respect to one or more other components of the PDGR.

Individual SPDEDs might, for instance, be arranged randomly, alphabetically, and/or ontologically with respect to one another along an axis of the PDGR. In at least one embodiment, a default SPDED arrangement, such as an alphabetical arrangement along the axis, might be set as the default SPDE PDGR display attribute. The default SPDED arrangement might then be changed to another type of arrangement as desired by utilizing the PDGR tool.

As yet another example, recall from above that in at least one embodiment, selecting an initial timeline width scale at block 206 might be performed as part of block 210. As such, in such an embodiment(s) a PDGR tool (e.g., the timeline PDGR tool) can be utilized to change a timeline width scale PDGR display attribute to select the initial timeline width scale and, in some circumstances, to then select one or more other timeline width scales to use, as desired. In at least one embodiment, a default initial timeline width scale might be set by the timeline width scale PDGR display attribute. The default initial timeline width scale might then be changed as desired by utilizing the PDGR tool.

Once the initial PDGR display attribute(s) is determined, at block 212, the CMD can be utilized to depict the PDGR based on the initial PDGR display attribute(s). This can be accomplished in any suitable way. For example, in accordance with at least one embodiment, the process, technique, or method 300 illustrated in FIG. 3 and described below can be utilized to accomplish block 212.

Note that the order in which the blocks of process, technique, or method 300 are described is not intended to be construed as a limitation, and any number of the described blocks or acts can be combined in any order and performed any number of times.

Furthermore, process, technique, or method 300 can be implemented in any suitable hardware, software, firmware, or combination thereof such that one or more computing devices can implement the process, technique, or method 300 and/or cause the process, technique, or method 300 to be implemented.

In at least one circumstance for instance, the process, technique, or method 300 can be stored on one or more computer-readable storage media as a set of computer-readable instructions that, when executed on a computing device(s), cause all or part of the process, technique, or method 300 to be performed.

Figure 3:
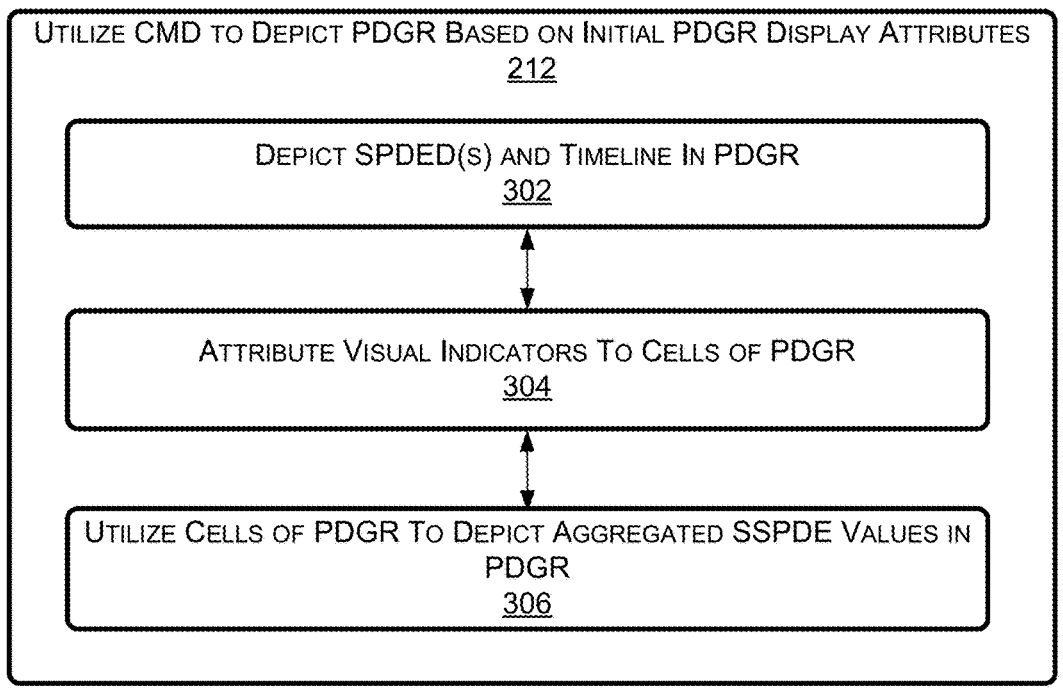

Referring now to FIG. 3, at block 302 the timeline and SPDEDs can be depicted in the PDGR. This can be accomplished in any suitable way. For example, as illustrated and described below, each PDGR cell can be depicted in the PDGR at the intersection of that cell's corresponding SPDED and time interval. Recall that in at least one embodiment, the SPDEDs selected at block 106 that are identified by the SPDED PDGR display attribute might be the SPDEDs.

The SPDED(s) can be organized in the PDGR in any suitable way. For example, the SPDEDs can be organized along a first axis of the PDGR. In at least one embodiment, the PDGR can be depicted in two dimensions with two axes, with the first axis being a vertical axis. Thus, the SPDEs might be arranged in the PDGR vertically (e.g. along the left side of the PDGR).

With respect to the relative arrangement (e.g., ordering) of individual SPDEDs, any type of arrangement criteria can be utilized. As noted above, in at least one embodiment the above-mentioned SPDE PDGR tool can be utilized to change an SPDE PDGR display attribute in order to arrange and/or rearrange individual SPDEDs. For example, individual SPDEDs might be arranged randomly along the first axis. As another example, SPDEDs might be arranged alphabetically (e.g. along the first axis) in the PDGR.

As yet another example, individual SPDEDs might be arranged in an ontological manner such that an SPDED is depicted proximal to one or more other related or associated SPDEDs in the PDGR. In other words, individual SPDEDs might be ontologically grouped with respect to one another in the PDGR (e.g. along the first axis).

In at least one embodiment for instance, individual clinical SPDEDs associated with a certain disease ontology might be ontologically grouped with respect to one another along the first axis of the PDGR such that these SPDEDs are organized and depicted relatively close (i.e., proximate) to one another. Depicting the SPDEDs in such an ontological manner can aid a clinician or other type of PDGR in visualizing individual PDGR cells that are associated with temporal clinical elements/events (i.e., with respect to the timeline) common to one or more certain clinical conditions (e.g., disease states or processes).

As another example, individual clinical SPDEDs might be arranged in the PDGR in a temporal manner such that an individual SPDED is depicted proximal to one or more other temporally related or associated SPDEDs in the graphical representation. Consider, for instance, individual clinical SPDEDs temporally grouped with respect to one another along an axis of the PDGR (e.g., the first axis) to aid a clinician or other type of user to visualize individual PDGR cells associated with clinical elements/events progressing toward, or following, the TZEOI and/or one or more other types of events.

Additionally, the timeline can also be depicted in the PDGR along a second axis of the PDGR. For instance, in an embodiment where the PDGR is depicted in two dimensions with the first axis being a vertical axis and the second axis being a horizontal axis, individual time intervals of the timeline can be arranged in the PDGR horizontally (e.g., along the top or bottom portion of the PDGR). As such, each PDGR cell can be depicted in the PDGR at the intersection of that cell's corresponding SPDED (arranged along the first axis) and that cell's corresponding time interval (arranged along the second axis).

Recall that at block 208, the CMD can be created by populating each CMD cell, and thus each PDGR cell, with at least one aggregated SSPDE value or a null value. As such, each PDGR cell can therefore be associated with a corresponding aggregated SSPDE value(s) or null value. In other words, each PDGR cell can have an aggregated SSPDE value(s) or null value.

Accordingly, at block 304 visual indicators can be attributed to cells of the PDGR (i.e., PDGR cells). This can be accomplished in any suitable way. For example, in at least one embodiment an individual visual indicator can be attributed to each individual corresponding PDGR cell based on that PDGR cell's aggregated SSPDE value or null value. In other words, one or more visual indicators representing or otherwise corresponding with an aggregated SSPDE value(s) or null value can be attributed to each cell of the PDGR.

Alternatively, in at least one other embodiment an individual visual indicator can be attributed only to each corresponding PDGR cell with an aggregated SSPDE. In such an embodiment, the individual visual indicator attributed to each such PDGR cell with an aggregated SSPDE value can be based on that aggregated SSPDE value. Those PDGR cells, if any, without an aggregated SSPDE value may not be attributed with a visual indicator.

Any type of visual indicator or visual indicators can be attributed to a PDGR cell. Non-limiting examples of such visual indicators include: color, characters such as numbers and/or text (e.g., representing the cell's assigned aggregated SSPDE value) with font one or more characteristics such as shape and/or size, cell and/or text border style, cell and/or character border shape and/or size, visual effects, and the like.

In at least one embodiment, various different visual indicators that each correspond to a certain aggregated SSPDE value, or range of aggregated SSPDE values, can be attributed to one or more PDGR cells. As mentioned above and illustrated below, one example type of visual indicator that can be attributed to a PDGR cell is color. Another example type of visual indicator of a type of visual indicator that can be attributed to a cell (e.g. in addition to color) is a character—such as one or more numbers and/or text characters that indicates (e.g. displays) at least one aggregated SSPDE value associated with that PDGR cell.

In some circumstances, individual PDGR cells that have a null value can be assigned a visual indicator(s) that makes those cells appear blank or empty. For example, such a PDGR cell might be assigned a visual indicator(s) that causes that cell to be depicted in the color white, and/or without a color.

When one or more different colors are attributed to multiple different PDGR cells, a heat map can be created to facilitate the recognition and assessment of characteristics and trends associated with individual PDGR cells, and thus with individual SPDEDs and corresponding time intervals.

For example, consider two sets of PDGR cells, a first PDGR cell set belonging to a first defined population, and a second PDGR cell set belonging to a second defined population. In a non-overlapping population view, each individual PDGR cell of each set can be attributed a shade of a color based upon that individual PDGR cell's aggregated SSPDE value. For example, in at least one embodiment a first PDGR cell of the first PDGR cell set might be attributed a relatively darker shade of a color (e.g., dark red) as compared to a second PDGR cell of a second PDGR cell set which might be attributed a relatively lighter shade of the color (e.g., pink) or a different color (e.g., green).

In an overlapping population view or partially overlapping population view, each individual PDGR cell of a population to display that overlaps with at least on other PDGR cell of at least one other population to display might be considered a composite PDGR cell of the at least two non-composite PDGR cells of each of the at least two populations.

With overlapping PDGR cells, each individual composite PDGR cell might be attributed a shade of a color based upon that individual composite PDGR cell's aggregated SSPDE value. For example, in at least one embodiment that individual composite PDGR cell's aggregated SSPDE value might be based on one or more of the respective aggregated SSPDE values of the at least two non-composite PDGR cells.

For example, without limitation, the individual composite PDGR cell's aggregated SSPDE value might be a sum, mean, average, comparative value representing the difference between the respective aggregated SSPDE values, or comparative value representing the similarity between the respective aggregated SSPDE values.

As a simple practical example, consider PDGR cells of a process PDGR that are composite PDGR cells of two defined populations to display in an overlapping population view. Each such composite PDGR cell might be associated with two underlying non-composite PDGR cells overlapping one another, each of the two non-composite cells having a corresponding aggregated SSPDE value. Accordingly, each such composite PDGR cell might have an aggregated SSPDE value that indicates a similarity between respective aggregated SSPDE values of the two non-composite PDGR cells of that composite PDGR. Each such composite PDGR cell might be attributed a color (e.g., green) based on that cell's aggregated SSPDE value.

More particularly for instance, one or more color values that are associated with relatively darker shades of that color (e.g., darker green) might be attributed to a composite PDGR cell with an aggregated SSPDE value that indicates a comparatively high degree of similarity between the respective aggregated SSPDE values of that cell's non-composite PDGR cells. One or more other color values that are associated with relatively lighter shades of that general color (e.g., light green, etc.) might be attributed to another composite PDGR cell with another aggregated SSPDE value that indicates a comparatively low degree of similarity between the respective aggregated SSPDE values of that cell's non-composite PDGR cells.

Similarly, one or more color values that are associated with relatively darker shades of another color (e.g., red) might be attributed to a composite PDGR cell with an aggregated SSPDE value that indicates a comparatively large difference between the respective aggregated SSPDE values of that cell's non-composite PDGR cells. One or more other color values that are associated with relatively lighter shades of that color (e.g., pink) might be attributed to another composite PDGR cell with another aggregated SSPDE value that indicates a comparatively small similarity between the respective aggregated SSPDE values of that cell's non-composite PDGR cells.

Consider, for instance, the above example in the context of a chemical synthesis process that includes the purposeful execution of certain chemical reactions in a certain order (i.e., sequence) to obtain a product without unacceptable characteristics. Such a process may be undertaken multiple times in repetition, as individual process cycles, in order to hopefully repeatedly obtain wanted products without unacceptable characteristics.

Furthermore, each of the individual steps and intermediary products or results (i.e., process elements) associated with each chemical synthesis process cycle may be associated with one or more risk points with respect to obtaining such a wanted product. For example, if a variance in a certain process or method element (e.g., a different product, a sequence of steps, and/or intermediary product) is inadvertently introduced into the process or method cycle, an unwanted product with one or more unacceptable characteristic(s) might be produced.

Accordingly, by utilizing the described techniques, process elements that are associated with a variance between a first and second group of chemical synthesis process cycles can be depicted and thus identified, recognized, and/or evaluated.

Individual visual indicators can be attributed to the individual PDGR cells by any suitable means. For example, in at least one embodiment a PDGR tool can be configured and utilized to perform some or all of this function based on the aggregated SSPDE values and/or null values of individual PDGR cells.

At block 306, the PDGR cells attributed a visual indicator(s) at block 304 can be utilized to depict the aggregated SSPDE values in the PDGR. In at least one embodiment, this can include depicting each such PDGR cell in accordance with the corresponding visual indicator(s) assigned to that cell. To facilitate the readers' understanding, an example PDGR is described below in which individual PDGR cells are depicted in accordance with their corresponding assigned visual color and/or character visual indicator to create a heat map.

In at least one embodiment, the PDGR can be configured to allow CAM of one or more PDGR cells to be depicted in response to user input. For example, the PDGR might be configured to depict (e.g., display in a window insert or pop-up window) a PDGR cell's CAM (if any) when a PDGR user hovers a pointer or other type of visual human interface device (HID) visual placement indicator over that PDGR cell.

Referring back to FIG. 1, once created at block 114, at block 116 the PDGR can be utilized to analyze the at least two populations. For example, in at least one embodiment the PDGR can be utilized to identify comparative population characteristics and/or possibilities associated with these populations. A population characteristic can be considered a similarity between the defined populations. For example, in the above example of a first population comprising a cohort of patients and a second smaller population comprising a sub-cohort of the cohort of patients, a similarity might be a relatively high abnormal lab value frequency for subjects within a certain time interval that is seen in both populations.

A population characteristic can also be considered a difference between the defined populations. In the above example for instance, a difference might be a relatively high abnormal lab value frequency associated with subjects within the time interval that is seen in the first population but not in the second smaller population.

A possibility can be considered a potential opportunity (e.g. benefit) and/or risk associated with at last one of the defined populations that is identified (e.g., noticed or discovered) by a PDGR user. For example, in the above example the PDGR user might observe the relatively high abnormal lab value frequency associated with subjects within the timeline time in the first population but not the second population.

The user might then identify a relatively high prevalence of a certain treatment during the time interval in the second population that is not found in the first population, and that may reasonably correlate with lowering subjects' lab values during that time interval. The user might identify the possibility of recommending treatment during that time interval for subjects of the first population as an opportunity, and not recommending treatment during that time interval as a risk.

In at least one embodiment, one or more PDGR tools can be configured and utilized to facilitate the analysis at block 116. For example a PDGR tool might be utilized to identify population characteristics and/or possibilities associated with the at least two populations.

Consider, for instance, a PDGR for two populations in which different colors have been attributed to different PDGR cells of the PDGR to create a heat map. A PDGR user might utilize a PDGR tool to change the arrangement of SPDEDs in the PDGR to an ontological arrangement in order to group similar SPDEDs close to one another along an axis of the PDGR, resulting in a visual aggregation of heat mapped PDGR cells. Such an arrangement might facilitate the PDGR user in visually identifying one or more visually distinguishable PDGR cells that are not visually similar to other surrounding PDGR cells. Such visually distinguishable PDGR cells might be representative of characteristics and/or possibilities associated with the two populations.

At block 118 one or more actions can be identified and/or implemented based on the analysis at block 116. For example, an action might be identified to address comparative population characteristics and/or possibilities identified at block 116. In some circumstances, this action might then be implemented.

Consider, for instance, a PDGR user who identifies a difference in an SPDED between a first population and a second population. A PDGR cell of the PDGR might have a difference value represented as a relatively dark color of that PDGR cell. The difference value might indicate that subjects of the first population have an average SSPDE value for that SPDED that is significantly lower than the average SSPDE value for subjects of the second population. If this lower average SSPDE value is favorable, then the PDGR user might identify other characteristics of the first population that could be associated with the lower average SSPDE value. One or more actions directed to achieving the other characteristics might then be identified and implemented with respect to subjects of the second population and/or one or more other populations.

Example Data Representation

Figure 5:
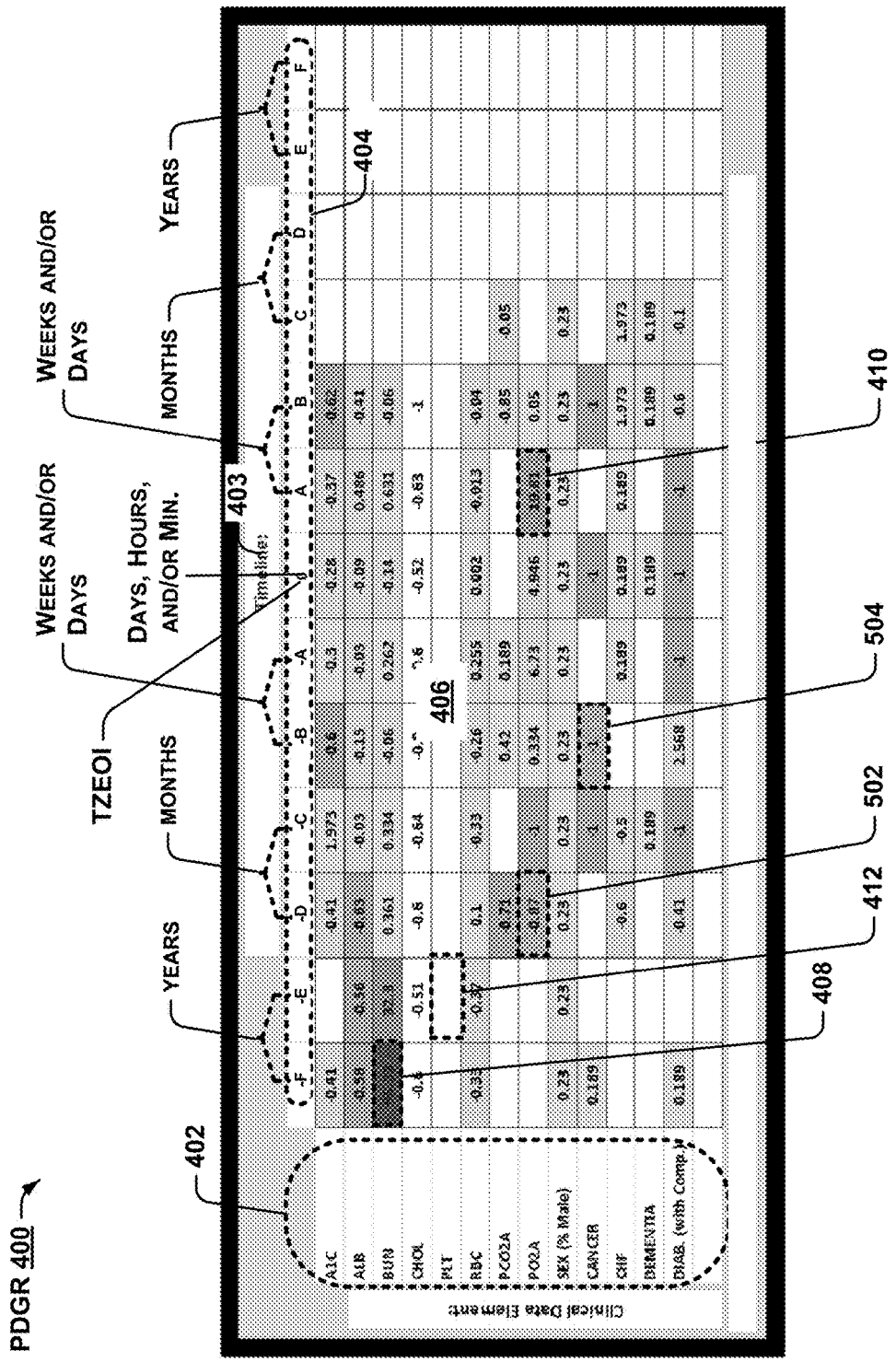

To facilitate the readers' understanding, FIGS. 4 and 5 illustrate a simple example of a data representation that is a PDGR, namely PDGR 400, which may be implemented in accordance with the described techniques.

While a graphical representation is illustrated and described in this example in the form of a two dimensional PDGR, it is to be appreciated and understood that other types of data representations with more than two dimensions (e.g. three dimensional PDGR) may be implemented and utilized in accordance with the described techniques.

A three dimensional PDGR, for instance, can be created and utilized to depict SPDEs and SSPDE values (e.g., SPDEs and/or SSPDE values with more than two dimensions) associated with three or more populations over time.

Without limitation, examples of other types of clinical representations with two or more dimensions include circular (e.g. doughnut shaped) representations for recurring or seasonal processes, so called "Word" and/or "Bubble" maps that can be distributed vertically and/or temporally to emphasize differences of sentinel events that identify one population from the other, and the like.

Note that in this example, the PDGR 400 is a clinical PDGR with an overlapping population view of two populations of interest to be depicted, namely a first and second defined population selected to be displayed in the PDGR 400. For example, the PDGR 400 might be associated with a population view PDGR display attribute that identifies these two populations and indicates an overlapping population view. As such, in at least one embodiment each PDGR cell of the PDGR 400 might be a composite PDGR cell of these two populations. This is not to be interpreted as limiting however, and in at least one embodiment a PDGR tool can be utilized to select any number of populations to be depicted and/or possible population views, such as a partially-overlapping population view and/or non-overlapping population view for instance.

In this example, one or more PDGR tools can be configured to create the PDGR, change the PDGR, and/or utilize the clinical PDGR 400 to identify one or more comparative population characteristics and/or possibilities for the populations. Alternatively or additionally, one or more PDGR tools can be configured and utilized to identify and/or implement one or more actions to address the one or more comparative population characteristics and/or possibilities.

Referring to FIG. 4, for purposes of discussion assume that here that the PDGR 400 is depicting multiple individual disparate SPDEs, namely SPDEDs 402, that are associated with two defined populations. The first population is the large cohort of patients (i.e., subjects) who have had hip surgery. In this example, assume that each such patient has had hip surgery. For purposes of discussion, this first patient population may be referred to herein as the control population.

The second population is the smaller cohort of patients (i.e., subjects) from the first cohort who had hip surgery and did not have an extended hospital stay after the hip surgery. For example, subjects of the second population may have not had a hospitalization period (if any) of less than four days after their hip surgery. For purposes of discussion, this second patient population may be referred herein as the case population.

Also assume that the SPDE of hip surgery has been selected as the TZEOI for PDGR 400. As such, the time zero for PDGR 400 can be defined as the TZEOI (hip surgery). A common reference point, which may be referred to as the time zero, can be utilized to define the timeline for the PDGR, namely timeline 403. As such, individual time intervals 404 of the timeline 403 can be sequentially organized in the PDGR 400 based upon the time zero (and thus the TZEOI).

Here in this example, note that SPDEDs 402 are sequentially arranged vertically along a column on the left side of the PDGR 400. This column on the left side of the PDGR 400 is along a first axis of the PDGR 400. In other words, here the PDGR 400 includes individual SPDEDs of the SPDEs 402 that are sequentially arranged along the first axis of the PDGR 400. Each of these SPDEDs can represent clinical characteristics associated with one or more individual patients in the control population and case population.

More particularly, in this example the SPDEDs 402 include an HbA1C element (A1C), Albumin element (ALB), blood urine nitrogen element (BUN), cholesterol element (CHOL), blood platelet count element (PLT), red blood cell element (RBC), partial pressure carbon dioxide element (PCO2A), partial pressure oxygen element (PO2A), sex (as a percentage of males) element (SEX (% Male)), cancer disease element (CANCER), congestive heart failure (CHF), dementia disease element (DEMENTIA), and a diabetes with complications disease element (DIAB. with complications).

Note that for ease of illustration and discussion, only thirteen individual SPDEDs are depicted as being included in SPDEDs 402. However, it is to be appreciated and understood that any number and type of SPDEDs can be included in a graphical representation, such as a PDGR, in accordance with the described techniques. Also note that the CANCER, CHF, DEMENTIA, and DIAB. (with complications) SPDEDs are examples of comorbitities that may be associated with one or more individual patients in the case population and/or control population.

Note that individual SPDEDs of SPDEDs 402 can be arranged sequentially along the first axis of PDGR 400 in any suitable way. Various non-limiting examples of individual SPDE arrangements and types of arrangement criteria, such as a random, alphabetical, and/or ontological arrangement along an axis are described above for instance.

In this example, note that individual time intervals 404 of the timeline 403 are sequentially arranged horizontally along a row in the top portion of the PDGR 400. This row is along a second axis of the PDGR 400. In other words, here the PDGR 400 includes individual time intervals of the timeline 403 that are sequentially arranged along the second axis of the PDGR 400.

Recall that the TZEOI for the PDGR 400 is the hip surgery event for patients in the case population and control population. Therefore, as explained above, each of the time intervals 404 of the timeline 403 can represent a time period (date and/or time) prior to the TZEOI (i.e., prior to the time zero), during the TZEOI (at time zero), or after the TZEOI (i.e., after the time zero). Therefore, for purposes of discussion, assume that here the time interval associated with the time zero (i.e., timeline interval marker 0 (zero)) represents a time period during the TZEOI.

Also assume that the individual sequentially depicted columns to the left of the time zero represent time intervals occurring prior to the TZEOI. Individual sequentially depicted columns to the right of the time zero represent time intervals occurring after the TZEOI.

As such, note that individual time intervals of time intervals 404 occurring prior to the TZEOI are each defined as a negative time interval, and individual time intervals occurring after the TZEOI are each defined as a positive time interval. In another words, the time interval markers −A, −B, −C, −D, −E, and −F each represent time spans that occurred before each patient's hip surgery procedure. The time interval markers A, B, C, D, E, and F, in turn, represent time intervals that occurred after each patient's hip surgery.

As explained above, in this example each of the time intervals −A, −B, −C, −D, −E, −F, 0, A, B, C, D, E, and F of the timeline 403 can be measured in, and thus defined by, a UOM that may, or may not, be the same type of unit of measure that defines one or more other time intervals.

More particularly for example, since comparably fewer SPDE events related to a patient are likely to happen in a time interval relatively farther away from the time zero (i.e., the TZEOI), time intervals relatively further away from time zero can be measured in comparatively larger UOMs, such as years, decades, etc.

Conversely, since comparably more SPDE events related to a patient are likely to happen in a time interval relatively close to the time zero, time intervals that are relatively closer to the time zero can be measured in comparatively smaller UOMs, such a months, weeks, days, etc.

Therefore, for purposes of discussion, assume that in this example, time intervals –F, –E, F, and E are each measured by a UOM of years, and time intervals –D, –C, D, and C are each measured by a UOM of months. Also assume that here, time intervals –A, –B, A, and B are each measured by a UOM of weeks and/or days, and time interval 0 is measured by a UOM of days, hours, and/or even minutes. As such, the timeline 403 is depicted in this example as a non-linear timeline. In other words, since each of the time intervals of 403 in this example are not measured by the same UOM, the timeline 403 is a non-linear timeline.

Continuing, note that in this example, the PDGR 400 includes multiple PDGR cells 406, each individual PDGR cell corresponding to a certain individual time interval of time intervals 403 and a certain individual SPDED of SPDEDs 402. As explained above, in at least one embodiment the PDGR cells 406 can be individual CMSD cells of a CMD that are depicted in the PDGR 400 as PDGR cells.

As also explained above, in at least one embodiment the PDGR cells 406 can be composite PDGR cells utilized to depict the aggregated SSPDE values. As such, here in this example note that some of the PDGR cells 406 depict an aggregated SSPDE values. More particularly, here the PDGR cell 408 is a composite PDGR cell that includes an aggregated SSPDE value 95.33 that is based on two aggregate SSPDE values of two underlying non-composite PDGR cells.

Additionally, note that here the PDGR cell 410 includes comparative population data that corresponds to the time interval A and the clinical data element PO2A. Note that the time interval A corresponds to a time span that occurred after each patient of interest's hip surgery. Also note that in this example, the PDGR cell 410 is a composite PDGR cell that includes an aggregated SSPDE value 19.81 that is based on two aggregate SSPDE values of two underlying non-composite PDGR cells.

Additionally, also note that here some of the PDGR cells 406 do not depict an aggregated SSPDE value and instead have been populated with a null value and are blank (i.e., blank cells). This may be for a variety of reasons. For example, for each of the two underlying non-composite PDGR cells corresponding to each of the blank cells may not be an obtained SSPDE value for the corresponding time interval and SPDED for such a blank cell. One example of such a blank cell is cell 412 that corresponds to the time interval –E and SPDED PLT.

Recall that visual indicia can be attributed to one or more cells of a graphical representation. As such, different visual indicators that each correspond to a certain aggregated SSPDE value, or aggregated SSPDE value range, can be attributed to certain PDGR cells with a certain aggregated SSPDE value. As described below, one example of a type of visual indicator that can be attributed to one or more cells is color. When multiple different colors are attributed to multiple different cells, a heat map can be created to facilitate the discernment and assessment of characteristics and trends associated with depicted SPDEDs and aggregated SSPDE values.

Accordingly, FIG. 5 illustrates the graphical representation 400 with individual cells of the PDGR cells 406 depicted with certain individual colors. In this example, assume that each PDGR cell is attributed with a certain color that corresponds to the aggregated SSPDE value, or null value, for that cell. In other words, assume that each individual cell of the PDGR cells 406 is depicted in the PDGR 400 with a color that corresponds to the aggregated SSPDE value or null value that that PDGE cell was populated with when the CMD was created at block 208.

As a practical example, assume that here individual PDGR cells of the PDGR cells 404 are composite PDGR cells of the two defined populations (i.e., the control population and the case population). In this regard, recall that in at least one embodiment individual composite PDGR cells of a PDGR can each have an aggregated SSPDE value that indicates a similarity or difference between respective aggregated SSPDE values of the two non-composite PDGR cells of that composite PDGR.

For example, assume that in this example that composite PDGR cells can be attributed with a green color. For purposes of discussion, these composite PDGR cells may be referred to as green cells. In this regard, the darker the shade of green of a green cell, the greater the degree of similarity between the respective aggregated SSPDE values of that green cell's non-composite PDGR cells. In other words, the darkness of a green cell's shade of green can correspond to the degree of similarity between the respective aggregated SSPDE values of that green cell's non-composite PDGR cells.

Similarly, assume that that in this example that other composite PDGR cells can be attributed with a red color. For purposes of discussion, these composite PDGR cells may be referred to as red cells. In this regard, the darker the shade of red of a red cell, the greater the degree of similarity between the respective aggregated SSPDE values of that red cell's two non-composite PDGR cells. In other words, the darkness of a red cell's shade of red can correspond to the degree of similarity between the respective aggregated SSPDE values of that red cell's non-composite PDGR cells.

Note that in this example, the PDGR cells 408 and 410 are examples of red cells. In other words, the PDGR cells 408 and 410 are red cells that are each attributed a shade of red that corresponds to their respective aggregated SSPDE values (95.3 and 19.81 respectively), and thus to the degree of similarity between the aggregated SSPDE values of each of their two underlying non-composite PDGR cells.

Similarly, also note that the PDGR cells 502 and 504 are examples of green cells. In other words, the PDGR cells 502 and 504 are green cells that are each attributed a shade of green that corresponds to their respective aggregated SSPDE values (−0.87 and −1 respectively), and thus to the degree of similarity between the aggregated SSPDE values of each of their two underlying non-composite PDGR cells.

Example System

The data visualization techniques described herein can be implemented in any suitable way. For example, recall that in at least one embodiment a PDGR and/or another type of data representation can be implemented in a system (e.g., a data representation system) of one or more computing devices and/or one or more networks. The system might include, for instance, the PDGR and one or more PDGR tools, such as the PDGRs and/or PDGR tools described herein.

Figure 6:
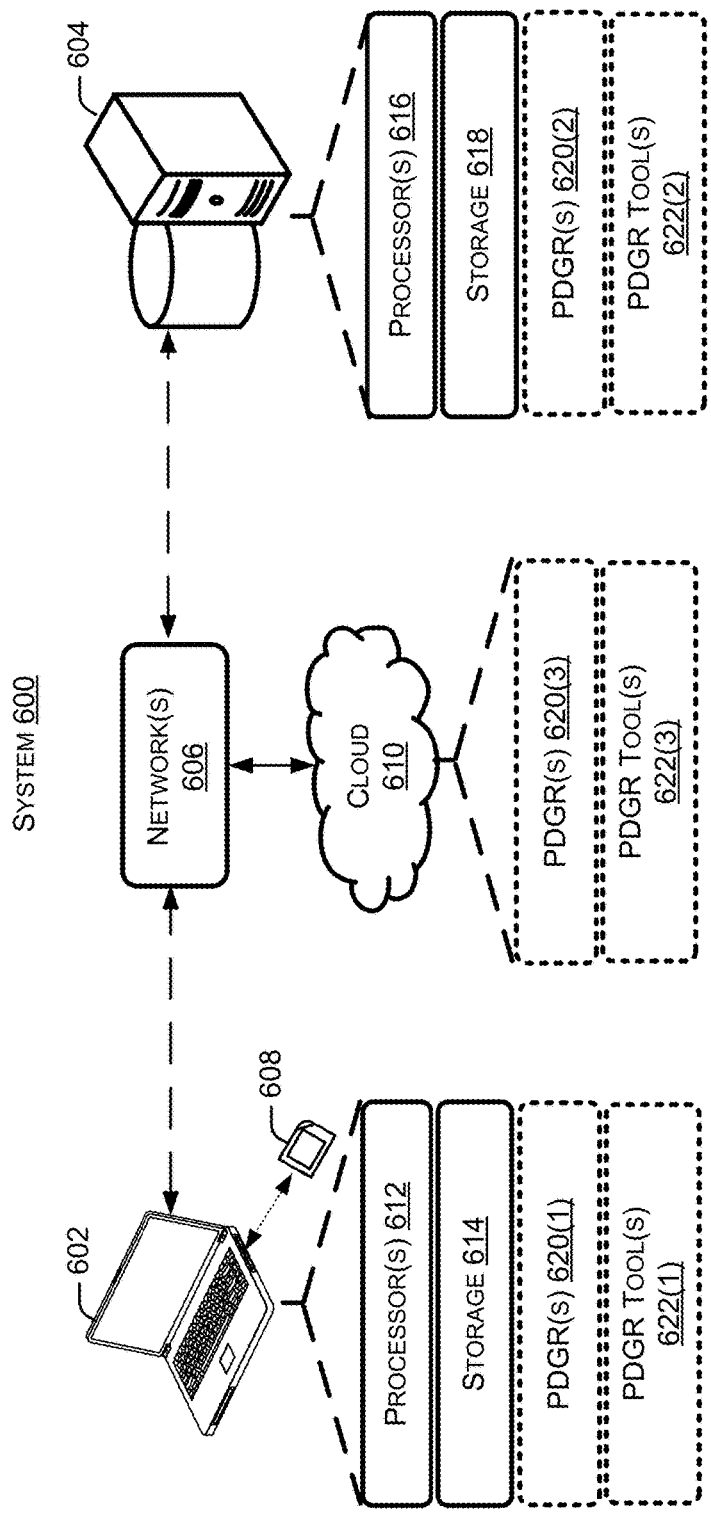
FIG. 6 illustrates an example system in which the described techniques and embodiments may be implemented, in accordance with at least one embodiment.

Accordingly, to facilitate the readers' understanding of such a system, FIG. 6 illustrates an example system 600 in accordance with at least one embodiment. In this example, the system 600 can include any number and type of computing devices, represented here as computing devices 602 and 604. These computing devices can function in a stand-alone or cooperative manner to implement the described techniques.

More particularly, in this example, the computing device 602 is shown embodied as a laptop computing device. Computing device 604, in turn, is shown embodied as a desktop or server computing device. However, this is not intended to be limiting, and it is to be appreciated and understood that the system 600 can include any number and/or type(s) of computing devices.

For example, the term computing device can mean any type of device or devices having some amount of processing capability. Examples of computing devices can include personal computers (desktop, portable laptop, etc.), mobile/cellular phones, smart phones, tablets, laptops, personal digital assistants, and/or any of various ever-evolving or yet to be developed types of computing devices.

In this example, computing devices 602 and 604 can indirectly and/or directly exchange data via one or more network(s) 606 and/or by any other suitable means, such as via external storage 608 for instance. Without limitation, network(s) 606 can include one or more local area networks (LANs), wide area networks (WANs), the Internet, and/or the like. Examples of external storage 608 can include optical storage devices (e.g., CDs, DVDs etc.) and flash storage devices (e.g., memory sticks or memory cards), etc.

Additionally or alternatively, computing devices 602 and/or 604 can exchange data with other computing-related resources associated with the cloud 610, for example via network(s) 606. As used herein, the cloud 610 can refer to computing-related resources/functionalities that can be accessed via network(s) 606, although the location of these computing resources and functionalities may not be readily apparent.

Here, computing devices 602 and 604 can each include a processor(s) (i.e., central processing unit(s)) and storage. More particularly, here computing device 602 can include processor(s) 612 and storage 614. Similarly, computing device 604 can include processor(s) 616 and storage 618. Processor(s) 612 and 616 can be configured and utilized to execute data in the form of computer-readable instructions to provide the functionality described herein.

Data, such as computer-readable instructions, can be stored on storage 614 and/or 618. Storage 614 and/or 618 can include one or more of volatile or non-volatile memory, hard drives, optical storage devices (e.g., CDs, DVDs etc.), or the like.

Devices 602 and 604 can also be configured to receive and/or generate data in the form of computer-readable instructions from one or more other storages, such as the external storage 608 for instance. These computing devices may also receive data in the form of computer-readable instructions over network(s) 606 that are then stored on the computing device(s) for execution by the processor(s).

As used herein, the term "computer-readable media" can include transitory and non-transitory instructions. In contrast, the term "computer-readable storage media" excludes transitory instances. Computer-readable storage media can include "computer-readable storage devices". Examples of computer-readable storage devices include volatile storage media, such as RAM, and non-volatile storage media, such as hard drives, optical discs, flash memory, and the like.

Recall that in at least one embodiment, as described above, a system such as the system 600 can include one or more PDGR tools, such as the one or more PDGR tools described herein. Accordingly, here in this example, computing device 602 is shown as being configured to implement at least part of one or more PDGRs 620 (i.e., as PDGR(s) 620(1)) and least part of one or more PDGR tools 622 (i.e., as PDGR tool(s) 622(1)).

Computing device 604 is also shown as being configured to implement at least part of the PDGR(s) 620 (i.e., as PDGR(s) 620(2)) and least part of one or more PDGR tools 622 (i.e., as PDGR tool(s) 622(2)).

Additionally, at least part of the PDGR(s) 620 and/or PDGR tool(s) 622 are shown in this example as being implementable by one or more distributed computing resources of the cloud 610 (i.e., as PDGR(s) 620(3) and PDGR tool(s) 622(3) respectively).

CONCLUSION

Data visualization techniques are described for representing population data for a relatively large number of subjects associated with multiple populations. In accordance with these techniques, a graphical representation can be created to represent population data elements and/or population data values for the populations over time. The graphical representation can be utilized to analyze the populations, and potentially identify and/or implement one or more actions based on the analysis.

The invention claimed is:

1. A method comprising:
defining at least two populations with subjects; and
creating a population data graphical representation (PDGR) to identify one or more similarities or differences between the at least two populations by representing heterogeneous population data for the at least two populations over time, creating the PDGR comprising:
selecting individual disparate population data elements of the heterogeneous population data to be displayed in the PDGR;
utilizing subject-specific population data element (SSPDE) values associated with the individual disparate population data elements to define a timeline for the PDGR, the timeline comprising multiple time intervals;
utilizing the SSPDE values to calculate individual aggregated SSPDE values for individual cells of a cell matrix dataset (CMD);
populating the individual cells of the CMD with the individual aggregated SSPDE values;
determining one or more PDGR display attributes based on the individual aggregated SSPDE values;
depicting the individual disparate population data elements, the timeline, and the individual cells of the CMD in the PDGR based on the one or more PDGR display attributes, each individual cell of the CDM corresponding to one of the individual disparate population date elements and one of the multiple time intervals;
depicting a composite cell in the PDGR to represent overlapping individual cells of the CMD, the composite cell corresponding to a same individual disparate population data element and a same time interval of the multiple time intervals, depicting the composite cell comprising:
  calculating a composite cell aggregated SSPDE value for the composite cell based on a first individual aggregated SSPDE value corresponding to a first population of the at least two populations and a second individual aggregated SSPDE value corresponding to a second population of the at least two populations; and
  attributing a visual indicator to the composite cell based on the composite cell aggregated SSPDE value, the visual indicator indicating a difference or similarity between the first individual aggregated SSPDE value and the second individual aggregated SSPDE value; and
utilizing the PDGR to analyze the at least two populations.

2. The method of claim 1, wherein the timeline comprises a non-linear timeline.

3. The method of claim 1, wherein to define the timeline comprises:
  calculating timeline time interval values (TIVs) for the multiple time intervals;
  assigning a first unit of measure (UOM) to at least one time interval of the multiple time intervals; and
  assigning a second UOM to at least one other time interval of the multiple time intervals, wherein the second UOM is different than the first UOM.

4. The method of claim 3, further comprising:
  calculating SSPDE time interval values (TIVs) for the SSPDE values; and
  utilizing the SSPDE TIVs and the timeline TIVs to map each SSPDE value to a corresponding time interval of the multiple time intervals.

5. The method of claim 3, wherein depicting the individual disparate population data elements, the timeline, and the individual cells of the CMD in the PDGR comprises:
  attributing individual visual indicators to one or more of the individual cells of the CMD based at least in part on one or more of the individual aggregated SSPDE values; and
  utilizing the individual cells of the CMD to depict the one or more aggregated SSPDE values.

6. The method of claim 1, wherein the PDGR comprises a clinical PDGR depicted in two dimensions, and wherein the individual disparate population data elements are arranged ontologically with respect to one another along an axis of the PDGR.

7. One or more non-transitory computer-readable storage media having instructions stored thereon that, when executed by a computing device, cause the computing device to perform acts comprising:
  obtaining population data comprising individual disparate population data elements and subject-specific population data element (SSPDE) values for at least two populations;
  defining a non-linear timeline comprising multiple time intervals, at least one time interval of the multiple time intervals measured in a first unit of measure (UOM) and at least one other time interval of the multiple time intervals measured in a second UOM different from the first UOM;
  utilizing the SSPDE values to calculate individual aggregated SSPDE values for individual cells of a cell matrix dataset (CMD);
  populating the individual cells of the CMD with the individual aggregated SSPDE values;
  determining one or more display attributes based on the individual aggregated SSPDE values; and
  depicting the individual disparate population data elements, the multiple time intervals, and the individual cells of the CMD in a graphical representation based on the one or more display attributes, each individual cell of the individual cells of the CMD corresponding to one of the individual disparate population data elements and one corresponding time interval of the multiple time intervals;
  depicting a composite cell in the graphical representation to represent overlapping individual cells of the CMD, the composite cell corresponding to a same individual disparate population data element and a same time interval of the multiple time intervals, depicting the composite cell comprising:
    calculating a composite cell aggregated SSPDE value based on a first individual aggregated SSPDE value corresponding to a first population of the at least two populations and a second individual aggregated SSPDE value corresponding to a second population of the at least two populations; and
    attributing a visual indicator to the composite cell based on the composite cell aggregated SSPDE value, the visual indicator indicating a difference or similarity between the first individual aggregated SSPDE value and the second individual aggregated SSPDE value.

8. The one or more non-transitory computer-readable storage media of claim 7, wherein the population data comprises heterogeneous population data.

9. The one or more non-transitory computer-readable storage media of claim 7, wherein depicting the individual disparate population data elements, the multiple time intervals, and the individual cells of the CMD in the graphical representation comprises:
  depicting the individual disparate population data elements along a first axis of the graphical representation; and
  depicting the multiple time intervals along a second axis of the graphical representation.

10. The one or more non-transitory computer-readable storage media of claim 9, wherein the individual disparate population data elements are arranged alphabetically or ontologically with respect to one another along the first axis.

11. The one or more non-transitory computer-readable storage media of claim 7, further comprising changing the at least one time interval to the second UOM or to a third UOM, wherein the third UOM is different from the first UOM.

12. The one or more non-transitory computer-readable storage media of claim 7, further comprising utilizing the graphical representation to analyze the at least two populations.

13. The method of claim 1, further comprising providing an overlapping population view or partially overlapping population view for the at least two populations.

14. A system comprising:
  one or more computing devices and a graphical representation, the system configured to:
  obtain population data comprising individual disparate population data elements and subject-specific population data element (SSPDE) values for at least two populations;
  define a non-linear timeline comprising multiple time intervals, at least one time interval of the multiple time intervals measured in a first unit of measure (UOM)

and at least one other time interval of the multiple time intervals measured in a second UOM different from the first UOM;

utilize the SSPDE values to calculate individual aggregated SSPDE values for individual cells of a cell matrix dataset (CMD);

populate the individual cells of the CMD with the individual aggregated SSPDE values;

determine one or more display attributes based on the individual aggregated SSPDE values; and depict the individual disparate population data elements, the multiple time intervals, and the individual cells of the CMD in the graphical representation based on the one or more display attributes, each individual cell of the individual cells of the CDM corresponding to one of the individual disparate population data elements and one corresponding time interval of the multiple time intervals;

depict a composite cell in the graphical representation to represent overlapping individual cells of the CMD, the composite cell corresponding to a same individual disparate population data element and a same time interval of the multiple time intervals, to depict the composite cell comprising:

calculate a composite cell aggregated SSPDE value based on a first individual aggregated SSPDE value corresponding to a first population of the at least two populations and a second individual aggregated SSPDE value corresponding to a second population of the at least two populations; and attribute a visual indicator to the composite cell based on the composite cell aggregated SSPDE value, the visual indicator indicating a difference or similarity between the first individual aggregated SSPDE value and the second individual aggregated SSPDE value.

15. The system of claim 14, wherein the population data comprises heterogeneous population data.

16. The system of claim 14, wherein to depict the individual disparate population data elements, the multiple time intervals, and the individual cells of the CMD in the graphical representation comprises:

depicting the individual disparate population data elements along a first axis of the graphical representation; and depicting the multiple time intervals along a second axis of the graphical representation.

17. The system of claim 16, wherein the individual disparate population data elements are arranged alphabetically or ontologically with respect to one another along the first axis.

18. The system of claim 14, wherein the system is configured to change the at least one time interval to the second UOM or to a third UOM, wherein the third UOM is different from the first UOM.

19. The system of claim 14, wherein the system is configured to utilize the graphical representation to analyze the at least two populations.

* * * * *